US 007666883B2

(12) United States Patent
Narender et al.

(10) Patent No.: US 7,666,883 B2
(45) Date of Patent: Feb. 23, 2010

(54) ANTIMALARIAL BAYLIS-HILLMAN ADDUCTS AND A PROCESS FOR THE PREPARATION THEREOF

(75) Inventors: Puli Narender, Hyderabad (IN); Banda Gangadasu, Hyderabad (IN); Uppalanchi Srinivas, Hyderabad (IN); Mettu Ravinder, Hyderabad (IN); Sriramoju Bharat Kumar, Hyderabad (IN); Chilukuri Ramesh, Hyderabad (IN); Vaidya Jayathirtha Rao, Hyderabad (IN); Janaswamy Madhusudhan Rao, Hyderabad (IN)

(73) Assignee: Council of Scientific and Industrial Research, New Delhi (IN)

( * ) Notice: Subject to any disclaimer, the term of this patent is extended or adjusted under 35 U.S.C. 154(b) by 421 days.

(21) Appl. No.: 11/366,672

(22) Filed: Mar. 3, 2006

(65) Prior Publication Data

US 2007/0117822 A1    May 24, 2007

Related U.S. Application Data

(63) Continuation of application No. PCT/IN2005/000397, filed on Dec. 2, 2005.

(30) Foreign Application Priority Data

Sep. 12, 2005  (IN) .................. 2462/DEL/2005

(51) Int. Cl.
*A61K 31/44* (2006.01)
*C07D 213/84* (2006.01)

(52) U.S. Cl. .................. 514/345; 514/277; 546/290; 546/301; 546/339

(58) Field of Classification Search .................. None
See application file for complete search history.

(56) References Cited

U.S. PATENT DOCUMENTS 6,479,660 B1 * 11/2002 Ugwuegbulam et al. .... 546/153

OTHER PUBLICATIONS

Narender et al, Tetrahedron, vol. 62, Issue 5, Jan. 30, 2006, pp. 954-959.*
Segheraert. et al. J.Med.Chem. 46, 2003, pp. 542-547.*

* cited by examiner

*Primary Examiner*—Zinna N Davis
(74) *Attorney, Agent, or Firm*—DLA Piper LLP (US)

(57) ABSTRACT

The present invention is directed towards the synthesis of novel and new chloropyridine skeleton based compounds and these are Bayllis Hillman adducts having a remarkable in vitro anti-malarial activity. These compounds have been found to possess anti-malarial activity against chloroquine sensitive and chloroquine resistant *Plasmodium falciparum*. The anti-malarial compounds of the present invention inhibit the mature schizonts in vitro.

34 Claims, No Drawings

ANTIMALARIAL BAYLIS-HILLMAN ADDUCTS AND A PROCESS FOR THE PREPARATION THEREOF

CROSS REFERENCE TO RELATED APPLICATIONS

This application is a continuation application of International Application No. PCT/IN05/00397, filed Dec. 2, 2005, and Indian Patent Application No. 2462/DEL/2005, filed Nov. 22, 2005, the entire contents of each of which being hereby incorporated by reference.

FIELD OF THE INVENTION

The present invention relate to a novel Bayllis Hillman adduct which are having a remarkable in vitro anti-malarial activity against chloroquine sensitive and chloroquine resistance *Plasmodium falciparum* and a process for the preparation thereof.

BACKGROUND OF THE INVENTION

Malaria is one of the world's leading killer infectious diseases. Although almost a third of the Earth's population is considered to be at risk from this disease, about 90% of infections and deaths occur in Africa (Trigg, P. I., and Wernsdorfer, W. H., Parasitologia: (1999) 41, 329-332), contributing significantly to underdevelopment and poverty on this continent (Gallup, J. L., and Sachs, J. D., Am. J. Trop. Med. Hyg: (2001) 64s, 85-96). The estimated 300 million cases that occur per year result in considerable morbidity (e. g. fever, malaise, anorexia, anemia) and mortality of over 2 million children under age group of five (World malaria situation in 1994 part I. Wkly Epidemiol rec: (1997) 72, 269-274. The intracellular protozoal parasite *Plasmodium falciparum*, accounts for greater than 95% of the malarial deaths. An important contributor to the increase in incidence of malaria over the past 30 years has been the development of resistance of the malarial parasite to quinoline containing antimalarials such as chloroquine and quinine (Barat, L. M., and Boland, P. B., Drug resistance among malaria and other parasites. Infet Dis Clin North Am: (1997) 11 (4), 969-987). In addition, it has been recognized that a number of complications, such as anemia, failure to gain weight and immunosuppression associated with malaria infection continue to occur for weeks and over months after the parasites are cleared from the body (Ho, M., Webster, H. K., and Looareesuwan, S. Antigen-specific immunosuppression in human malaria due to *plasmodium falciparum*. J. Infect Dis: (1986) 153, 763-771; McGregor, A., and Barr, M. Antibody response to tetanus toxoid inoculation in malarious and non-malarious Gambian children. Trans R Soc Trop Med hyg: (1962) 56, 364-367; Bradley-Moore, A. M., Greenwood, B. M. and Bradley, A. K. Malaria chemoprophylaxis with chloroquine in young Nigerian children. II. Effect on immune response to vaccination. Ann Trop Med Parasitol: (1985) 79, 563-573). For the majority of their life-cycle in humans, malaria parasites live in red blood cells. Within the erythrocytes, the parasites feed on hemoglobin, digesting the protein and releasing the heme. The heme which is released as the by-product of hemoglobin is toxic compound to the parasite. The malarial parasite having a unique heme detoxication mechanism that the heme is converted to non-toxic heme polymer hemozoin (malaria pigment) within the food vacuole (Rudzinska, M. A., Trager, W. and Bray, R. S. Pinocytic uptake and the digestion of hemoglobin in malaria parasites. J. Protozool: (1965) 12(4), 563-576). Trager, W; Jensen, J. B. Science, (1976), 193, 674) that serves to protect the parasite from potentially toxic free heme, as well as to induce pathology in the infected host. Overtime, the intraerythrocytic parasite exhausts this energy and protein supply and then begins next stage of life cycle. Through a series of DNA and membrane divisions, trophozoites converted to mature schizonts. Schizonts-containing erythrocytes rupture, each releasing 6 to 24 merozoites and one large 'garbage bag' containing polymerized hemozoin. It is this process that produces febrile clinical attack. The released merozoites invade more erythrocytes to continue the cycle, which proceeds until death of the host or modulation by drugs or acquired immunity. The 2-chloropyridine based Baylis Hillman adducts and 4-quinolino-methanols are reported to be antimalarial agents. These classes of compounds are particularly acting on erythrocytic stage of the parasite.

The following references are examples for the synthesis of and biological evaluation of some of the antimalarial agents. These prior arts contain useful information and discussion on the preparation and properties of antimalarial agents.

U.S. Pat. No. 6,627,641 (2003) reported the synthesis and use of naphthylisoquinoline alkaloids and their pharmaceutical formulation as efficient antmalarial agents.

U.S. Pat. No. 6,479,660 (2000) reported the synthesis and use of quinoline compounds as antimalarial drugs.

Sujatha, V. B. et. al. *Bioorg & Med. Chem. Lett*, 9, 731-736 (1999) reported the antimalarial activity of 3-hydroxy alkyl-2-methylene-propionic acid derivatives.

U.S. Pat. No. 6,689,777 (2004) reported the synthesis of novel substituted naphthothiozolium, aromatic guanylhydrazones and other compounds and compositions having antimalarial activity.

Donald J. Krogstad. et al., *Science*, 238, 1283-1285 (1987) reported the mechanism of chloroquine resistance in plasmodium.

U.S. Pat. No. 6,693,217 (2004) reported the synthesis of N, N1-substituted asymmetrical imidodicarbonimidic diamides as antimalarial agents.

Arnulf Dorn et al., *Nature* 374, 269-371 (1995) reported the process of heme polymerization and mechanism of action of chloroquine.

U.S. Pat. No. 2004/0180913 (2004) reported the synthesis of 2,4-diaminopyrimidine derivatives and their use as antimalarial agents by inhibiting dihydrofolate reductase (DHFR-Inhibitors)

Christian Segheraert. et al. *J. Med. Chem.* 46, 542-547 (2003) reported the synthesis and antimalarial activity of $N^1$-(7-chloro-4quinolyl)-1,4bis(3-aminopropyl) piperazine derivatives.

OBJECTS OF THE INVENTION

One object of the present invention is to provide novel Baylis Hillman adducts based on the chloropyridine skeleton as anti malarial agents.

Another object of the present invention is to provide pharmaceutical composition comprising novel Baylis Hillman adducts as antimalarial agents.

Still another object of the present invention is to provide a process for the preparation of novel Baylis Hillman adduct based on the chloropyridine skeleton, as anti malarial agent.

SUMMARY OF THE INVENTION

The present invention is directed towards the synthesis of novel chloropyridine skeleton based compounds and these are Bayllis Hillman adducts having a remarkable in vitro anti-malarial activity. These compounds have been found to possess anti-malarial activity against chloroquine sensitive and chloroquine resistance *Plasmodium falciparum*. The anti-malarial compounds of the present invention inhibit the mature schizonts in vitro.

This invention meets the need for more efficient compounds against malaria, in particularly chloroquine resistance *plasmodium falciparum*. Accordingly present invention provides novel compounds based on chloropyridine skeleton of general structural formula 1. These are the Baylis Hillman reaction adducts having the general structure of formula I & II indicates total thirty seven (37) compounds which is represented below.

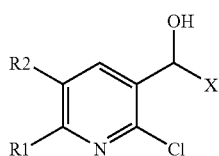

Formula 1

Ia: R1=H, R2=CH3, X=acrylonitrile; IIa: R1=H, R2=CH3, X=2-cyclopenten-1-one

Ib: R1=H, R2=C2H5, X=acrylonitrile IIb: R1=H, R2=C2H5, X=2-cyclopenten-1-one

Ic: R1=H, R2=Ph, X=acrylonitrile IIc: R1=H, R2=Ph, X=2-cyclopenten-1-one

Id: R1=COOMe, R2=H, X=acrylonitrile IId: R1=Ph, R2=CH3, X=2-cyclopenten-1-one

Ie: R1=H, R2=CH3, X=methyl acrylate IIe: R1=COOMe, R2=H, X=2-cyclopenten-1-one

If: R1=H, R2=Ph, X=methyl acrylate IIf: R1=Ph, R2=COOEt, X=2-cyclopenten-1-one

Ig: R1=H, R2=n-C5H11, X=acrylonitrile IIg: R1=H, R2=4-OMe-Ph, X=2-cyclopenten-1-one Ih: R1=Ph, R2=CH3, X=acrylonitrile IIh: R1=H, R2=CH3, X=2-cyclohexen-1-one Ii: R1=Ph, R2=COOEt, X=acrylonitrile IIi: R1=H, R2=C2H5, X=2-cyclohexen-1-one Ij: R1=H, R2=4-OMe-Ph, X=acrylonitrile IIj: R1=H, R2=Ph, X=2-cyclohexen-1-one Ik: R1=H, R2=C2H5, X=methylacrylate IIk: R1=Ph, R2=CH3, X=2-cyclohexen-1-one Il: R1=H, R2=n-C5H11, X=methylacrylate IIl: R1=COOMe, R2=H, X=2-cyclohexen-1-one Im: R1=Ph, R2=CH3, X=methylacrylate IIm: R1=Ph, R2=COOEt, X=2-cyclohexen-1-one In: R1=COOMe, R2=H, X=methylacrylate IIn: R1=H, R2=4-OMe-Ph, X=cyclohexen-1-one Io: R1=Ph, R2=COOEt, X=methylacrylate Ip: R1=H, R2=4-OMe-Ph, X=methylacrylate Iq: R1=H, R2=CH3, X=ethylacrylate Ir: R1=H, R2=C2H5, X=ethylacrylate Is: R1=H, R2=Ph, X=ethylacrylate It: R1=Ph, R2=CH3, X=ethylacrylate Iu: R1=COOMe, R2=H, X=ethylacrylate Iv: R1=Ph, R2=COOEt, X=ethylacrylate Iw: R1=H, R2=4-OMe-Ph, X=ethylacrylate

DETAILED DESCRIPTION OF THE INVENTION

Accordingly the present invention provides a novel chloro pyridine skelton based Baylis-Hillman adduct having the general formula

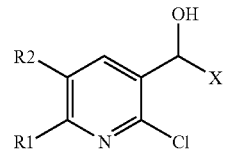

wherein

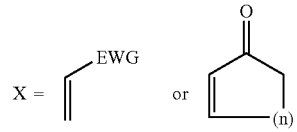

R1 is selected from the group consisting of hydrogen, phenyl and carbomethoxy; R2 is selected from the group consisting of hydrogen, alkyl, $CH_3$, $C_2H_5$, phenyl, $n-C_5H_{11}$, carboethoxy and p-OMe-Ph; EWG is an electron withdrawing group selected from the group consisting of CN, COOMe and COOEt.

In an embodiment of the present invention the novel chloro pyridine skelton based Baylis-Hillman adduct used comprising the compounds of general formula I & II

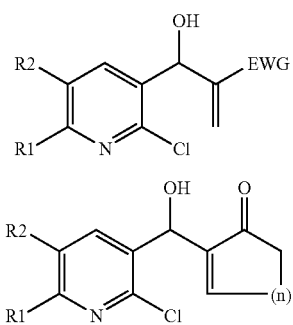

R1 is selected from the group consisting of hydrogen, phenyl and carbomethoxy; R2 is selected from the group consisting of hydrogen, alkyl, $CH_3$, $C_2H_5$, phenyl, $n-C_5H_{11}$, carboethoxy and p-OMe-Ph; EWG is an electron withdrawing group selected from the group consisting of CN, COOMe and COOEt.

In yet another embodiment the novel chloro pyridine skelton based Baylis-Hillman adduct obtained is in the form of derivatives, analogues or salt thereof.

In yet another embodiment the novel chloro pyridine skelton based Baylis-Hillman adduct obtained is selected from the group consisting of 2-[(2-Chloro-5-methylpyridine-3-yl)(hydroxy)methyl]acrylonitrile (Ia), 2-[(2-Chloro-5-ethylpyridine-3-yl)(hydroxy)methyl]acrylonitrile (Ib), 2-[(2-Chloro-5-phenylpyridine-3-yl)(hydroxy)methyl] acrylonitrile (Ic), methyl 6-chloro-5-(2-cyano-1-hydroxy allyl)2-pyridine carboxylate (Id), Methyl 2-[(2-chloro-5-methylpyridine-3-)(hydroxy)methyl]acrylate (Ie), Methyl 2-[(2-chloro-5-phenylpyridine-3-yl)(hydroxy)methyl]acrylate (If), 2-[(2-chloro-5-n-pentylpyridine-3-yl)(hydroxy)methyl] acrylonitrile (Ig), 2-[(2-Chloro-5-methyl-6-phenylpyridine-3-yl)(hydroxy)methyl]acrylonitrle (Ih), Ethyl 6-chloro-5-(2-cyano-1-hydroxy allyl)-2-phenyl-nicotinate (Ii), 2-[(2-Chloro-5-(4-methoxyphenyl)pyridine-3-yl)(hydroxy) methyl]acrylonitrile (Ij), Methyl 2-[(2-chloro-5-ethyl pyridine-3-yl)(hydroxy)methyl]acrylate (Ik), Methyl 2-[(2-chloro-5-n-pentylpyridine-3-yl)(hydroxy)methyl]acrylate (Il), Methyl 2-[(2-chloro-5-methyl-6-phenyl pyridine-3-yl)(hydroxy)methyl]acrylate (Im), Methyl 6-chloro-5-[1-hydroxy-2-(methoxycarbonyl)allyl]pyridine-2-carboxylate (In), Ethyl 6-chloro-5-(1-hydroxy-2-(methoxycarbonyl)allyl)-2-phenyl-nicotinate (Io), Methyl 2-[(2-chloro-5-(4-methoxyphenyl)pyridine-3-yl)(hydroxy)methyl]acrylate (Ip), Ethyl 2-[(2-chloro-5-methylpyridine-3-)(hydroxy)methyl]acrylate (Iq), Ethyl 2-[(2-chloro-5-ethyl pyridine-3-yl)(hydroxy)methyl]acrylate (Ir), Ethyl 2-[(2-chloro-5-phenyl pyridine-3-yl)(hydroxy)methyl]acrylate (Is), Ethyl 2-[(2-chloro-5-methyl-6-phenyl pyridine-3-yl)(hydroxy)methyl] acrylate (It), Methy-6-chloro-5-[1-hydroxy-2-(ethoxycarbonyl)allyl]pyridine-2-carboxylate (Iu), Ethyl 6-chloro-5-(1-hydroxy-2-(ethoxycarbonyl)allyl)-2-phenyl-nicotinate (Iv), Ethyl 2-[(2-chloro-5-(4-methoxyphenyl)pyridine-3-yl)(hydroxy)methyl]acrylate (Iw), 2-[(2-Chloro-5-methyl pyridine-3-yl)(hydroxy)methyl]cyclopent-2-en-1-one (IIa), 2-[(2-Chloro-5-ethyl pyridine-3-yl)(hydroxy)methyl]cyclopent-2-en-1-one (IIb), 2-[(2-Chloro-5-phenyl pyridine-3-yl)(hydroxy)methyl]cyclopent-2-en-1-one (IIc), 2-[(2-Chloro-5-methyl-6-phenyl pyridine-3-yl)(hydroxy)methyl] cyclopent-2-en-1-one (IId), Methyl-6-chloro-5-[hydroxy(5-oxo-1-cyclopentenyl)methyl]-2-pyridine carboxylate (IIe), Ethyl 6-chloro-5-[hydroxy(5-oxo-1-cyclopentenyl)methyl]-2-phenyl nicotinate (IIf), 2-[(2-Chloro-5-(4-methoxyphenyl) pyridine-3-yl)(hydroxy)methyl]cyclopent-2-en-1-one (IIg), 2-[(2-Chloro-5-methylpyridine-3-yl)(hydroxy)methyl]2-cyclohexene1-one (IIh), 2-[(2-Chloro-5-ethylpyridine-3-yl) (hydroxy)methyl]cyclohex-2-ene-1-one (IIi), 2-[(2-Chloro-5-phenyl pyridine-3-yl)(hydroxy)methyl]cyclohex-2-ene-1-one (IIj), Methyl 2-[(2-chloro-5-ethyl pyridine-3-yl) (hydroxy)methyl]acrylate (Ik), Methyl 6-chloro-5-[hydroxy (5-oxo-1-cyclohexenyl)methyl]-2-pyridine carboxylate (IIl), Ethyl 6-chloro-5-[hydroxy(5-oxo-1-cyclohexenyl)methyl]-2-phenyl nicotinate (IIm) and 2-[(2-Chloro-5-(4-methoxyphenyl)pyridine-3-yl)(hydroxy)methyl]cyclohex-2-en-1-one (IIn).

In yet another embodiment the novel chloro pyridine skelton based Baylis-Hillman adduct is active against chloroquine sensitive and chloroquine resistant *plasmodium falciparum* strains.

In yet another embodiment novel chloro pyridine skelton based Baylis-Hillman adduct exhibits an anti malarial activity against the erythrocytic stage of the malarial parasite.

The present invention further provides a pharmaceutical composition comprising novel anti malarial chloro pyridine skelton based Baylis-Hillman adduct, its derivatives, analogues or salt thereof optionally with pharmaceutically acceptable carriers, adjuvant and additives.

The present invention further provides a method for the treatment of malaria in a subject wherein a dose of 1-45 µg/ml and 1-115 µg/ml drug is administered for IC50 against chloroquine sensitive (CQS) *P. falciparum* strain to such subject for schizont maturation inhibition (SMI) and total parasite growth inhibition (PGI), for at least 24 and 48 hrs, respectively.

In yet another embodiment a dose of 25-125 µg/ml and 85-350 µg/ml drug is administered for IC90 against chloroquine sensitive (CQS) *P. falciparum* strain to such subject for schizont maturation inhibition (SMI) and total parasite growth inhibition (PGI), for at least 24 and 48 hrs, respectively.

In yet another embodiment a dose of 0.2-30 µg/ml and 5-15 µg/ml drug is administered for IC50 against chloroquine resistant *plasmodium falciparum* strain to such subject for schizont maturation inhibition (SMI) and total parasite growth inhibition (PGI), for at least 24 and 48 hrs, respectively.

In yet another embodiment a dose of 1-125 µg/ml and 25-300 µg/ml drug is administered for IC90 against chloroquine resistant *plasmodium falciparum* strain to such subject for schizont maturation inhibition (SMI) and total parasite growth inhibition (PGI), for at least 24 and 48 hrs, respectively.

The present invention further provides a process for the preparation of chloro pyridine skelton based Baylis-Hillman adduct having the general formula

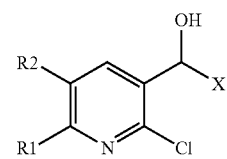

wherein

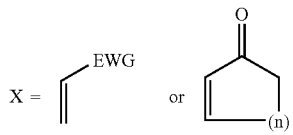

R1 is selected from the group consisting of hydrogen, phenyl and carbomethoxy; R2 is selected from the group consisting of hydrogen, alkyl, $CH_3$, $C_2H_5$, phenyl, n-$C_5H_{11}$, carboethoxy and p-OMe-Ph; EWG is an electron withdrawing group selected from the group consisting of CN, COOMe and COOEt, which comprises reacting 2-chloro-5 and/or 6-substituted 3-pyridine carboxyaldehyde with an activated alkene or cyclic enone, optimally in the presence of aqueous or non aqueous organic solvent, in the presence of a catalyst, at a temperature in the range of 20-30° C., washing the organic layer of the above said reaction mixture with water or brine solution, followed by drying and purification by known method to obtain the desired product.

In yet another embodiment the 2-chloro-5 and/or 6-substituted 3-pyridine carboxyaldehyde used is selected from the group consisting of 2-Chloro-5-methylpyridinecarboxaldehyde, 2-Chloro-5-ethylnicotinaldehyde, 2-Chloro-5-phenyl nicotinaldehyde, methyl6-chloro-5-formyl-2-pyridincarboxylate, 2-chloro-5-methyl nicotinaldehyde, 2-Chloro-5-phenylnicotinaldehyde, 2-chloro-5-pentylnicotinaldehyde, 2-Chloro-5-methyl-6-phenylnicotinaldehyde, 2-Chloro-5-ethoxyacetate)-6-phenylnicotinaldehyde, 2-Chloro-5-(4-methoxyphenyl)-nicotinaldehyde, 2-Chloro-5-ethylnicotinaldehyde, 2-Chloro-5-pentylnicotinaldehyde, 2-Chloro-5- methyl-6-phenylnicotin aldehyde, Methyl 6-chloro-5-formyl-2-pyridin carboxylate, 2-Chloro-5-ethoxyacetate)-6-phenylnicotinaldehyde, 2-Chloro-5-(4-methoxyphenyl)-nicotinaldehyde, 2-Chloro-5-methyl nicotinaldehyde, 2-Chloro-5-ethylnicotinaldehyde, 2-Chloro-5-phenylnicotin aldehyde, 2-Chloro-5-methyl-6-phenylnicotinaldehyde, Methyl 6-chloro-5-formyl-2-pyridincarboxylate, 2-Chloro-5-ethoxyacetate)-6-phenylnicotin aldehyde, 2-Chloro-5-(4-methoxyphenyl)nicotinaldehyde, 2-Chloro-5-methyl nicotinaldehyde, 2-Chloro-5-ethylnicotin aldehyde, 2-Chloro-5-phenylnicotinaldehyde, 2-Chloro-5-methyl-6-phenylnicotin aldehyde, Methyl 6-chloro-5-formyl-2-pyridincarboxylate, 2-Chloro-5-ethoxyacetate)-6-phenyl nicotinaldehyde, 2-Chloro-5-(4-methoxyphenyl)-nicotin aldehyde, 2-Chloro-5-methylnicotinaldehyde, 2-Chloro-5-ethylnicotinaldehyde, 2-Chloro-5-phenylnicotinaldehyde, 2-chloro-substituted-3-pyridinecarboxy aldehyde, methyl 6-chloro-5-formyl-2-pyridincarboxylate, 2-Chloro-5-ethoxyacetate)-6-phenyl nicotinaldehyde and 2-Chloro-5-(4-methoxyphenyl)-nicotinaldehyde.

In yet another embodiment the activated alkene used is selected from the group consisting of acrylonitrile, methyl acrylate and ethyl acrylate.

In yet another embodiment the cyclic enone used is selected from 2-cyclopenten-1-one and 2-cyclohexen-1-one.

In yet another embodiment the catalyst used is selected from di azabicylooctane (DABCO) and imidazole.

In yet another embodiment the organic solvent used is selected from the group consisting of methanol, ethanol, acetonitrile, tetrahydrofuran, dimethylsulphoxide (DMSO) and dimethylformamide (DMF) 1,4-dioxane, chloroform and sulpholane.

In yet another embodiment the molar ratio of 2-chloro-5 and/or 6-substituted 3-pyridine carboxyaldehyde to activated alkene or cyclic enone used is in the range of 1:1 to 1:8.

In yet another embodiment the molar ratio of 2-chloro-5 and/or 6-substituted 3-pyridine carboxyaldehyde to activated alkene in the reaction mixture used is in the range of 1:5 to 1:8.

In yet another embodiment the molar ratio of 2-chloro-5 and/or 6-substituted 3-pyridine carboxyaldehyde to cyclic enone used is preferably in the range of 1:1 to 1:2.

In yet another embodiment the molar ratio of 2-chloro-5 and/or 6-substituted 3-pyridine carboxyaldehyde to catalyst used is in the range of 1:1 to 1:2.

In yet another embodiment the molar ratio of activated alkene to catalyst used is in the range of 1:1 to 1:2.

In yet another embodiment the reaction mixture of aldehyde and alkene used is diluted with diethyl ether and is followed by washing with water and drying the resultant organic layer over sodium sulphate before subjected to purification by column chromatography.

In yet another embodiment the reaction mixture of aldehyde and cyclic-enone is taken into chloroform and the organic layer is washed with brine solution before drying and purification by known method to obtain the desired product.

In yet another embodiment the reaction time between aldehyde and cyclic-enone used is in the range of 20-40 minutes.

In yet another embodiment the yield of the product chloro pyridine skelton based Baylis-Hillman adduct is in the range of 85-98% without forming side products.

In another embodiment, the product chloro pyridine skelton based Baylis-Hillman adduct obtained is selected from the group consisting of 2-[(2-Chloro-5-methyl pyridine-3-yl)(hydroxy)methyl]acrylonitrile (Ia), 2-[(2-Chloro-5-ethyl pyridine-3-yl)(hydroxy)methyl]acrylonitrile (Ib), 2-[(2-Chloro-5-phenylpyridine-3-yl)(hydroxy)methyl]acryloni-
trile (Ic), methyl 6-chloro-5-(2-cyano-1-hydroxy allyl) 2-pyridine carboxylate (Id), Methyl 2-[(2-chloro-5-methylpyridine-3-) (hydroxy)methyl]acrylate (Ie), Methyl 2-[(2-chloro-5-phenylpyridine-3-yl)(hydroxy)methyl]acrylate (If), 2-[(2-chloro-5-n-pentylpyridine-3-yl)(hydroxy) methyl]acrylonitrile (Ig), 2-[(2-Chloro-5-methyl-6-phenylpyridine-3-yl)(hydroxy)methyl]acrylonitrle (Ih), Ethyl 6-chloro-5-(2-cyano-1-hydroxy allyl)-2-phenyl-nicotinate (Ii), 2-[(2-Chloro-5-(4-methoxyphenyl)pyridine-3-yl)(hydroxy)methyl]acrylonitrile (Ij), Methyl 2-[(2-chloro-5-ethylpyridine-3-yl)(hydroxy)methyl]acrylate (Ik), Methyl 2-[(2-chloro-5-n-pentyl pyridine-3-yl)(hydroxy)methyl] acrylate (Il), Methyl 2-[(2-chloro-5-methyl-6-phenyl pyridine-3-yl)(hydroxy)methyl]acrylate (Im), Methyl 6-chloro-5-[1-hydroxy-2-(methoxycarbonyl)allyl]pyridine-2-carboxylate (In), Ethyl 6-chloro-5-(1-hydroxy-2-(methoxycarbonyl)allyl)-2-phenyl-nicotinate (Io), Methyl 2-[(2-chloro-5-(4-methoxyphenyl)pyridine-3-yl)(hydroxy) methyl]acrylate (Ip), Ethyl 2-[(2-chloro-5-methyl pyridine-3-)(hydroxy)methyl]acrylate (Iq), Ethyl 2-[(2-chloro-5-ethyl pyridine-3-yl)(hydroxy)methyl]acrylate (Ir), Ethyl 2-[(2-chloro-5-phenyl pyridine-3-yl)(hydroxy)methyl]acrylate (Is), Ethyl 2-[(2-chloro-5-methyl-6-phenyl pyridine-3-yl)(hydroxy)methyl]acrylate (It), Methy-6-chloro-5-[1-hydroxy-2-(ethoxycarbonyl)allyl]pyridine-2-carboxylate (Iu), Ethyl 6-chloro-5-(1-hydroxy-2-(ethoxycarbonyl)allyl)-2-phenyl-nicotinate (Iv), Ethyl 2-[(2-chloro-5-(4-meth oxyphenyl)pyridine-3-yl)(hydroxy)methyl]acrylate (Iw), 2-[(2-Chloro-5-methyl pyridine-3-yl)(hydroxy)methyl]cyclopent-2-en-1-one (IIa), 2-[(2-Chloro-5-ethyl pyridine-3-yl) (hydroxy)methyl]cyclopent-2-en-1-one (IIb), 2-[(2-Chloro-5-phenyl pyridine-3-yl)(hydroxy)methyl]cyclopent-2-en-1-one (IIc), 2-[(2-Chloro-5-methyl-6-phenyl pyridine-3-yl) (hydroxy)methyl]cyclopent-2-en-1-one (IId), Methyl-6-chloro-5-[hydroxy(5-oxo-1-cyclopentenyl)methyl]-2-pyridinecarboxylate (IIe), Ethyl 6-chloro-5-[hydroxy(5-oxo-1-cyclopentenyl)methyl]-2-phenyl nicotinate (IIf), 2-[(2-Chloro-5-(4-methoxyphenyl)pyridine-3-yl)(hydroxy) methyl]cyclopent-2-en-1-one (IIg), 2-[(2-Chloro-5-methyl pyridine-3-yl)(hydroxy)methyl]2-cyclohexene1-one (IIh), 2-[(2-Chloro-5-ethyl pyridine-3-yl)(hydroxy)methyl]cyclohex-2-ene-1-one (IIi), 2-[(2-Chloro-5-phenyl pyridine-3-yl) (hydroxy)methyl]cyclohex-2-ene-1-one (IIj), Methyl 2-[(2-chloro-5-ethyl pyridine-3-yl)(hydroxy)methyl]acrylate (Ik), Methyl 6-chloro-5-[hydroxy(5-oxo-1-cyclohexenyl)methyl]-2-pyridine carboxylate (III), Ethyl 6-chloro-5-[hydroxy (5-oxo-1-cyclohexenyl)methyl]-2-phenyl nicotinate (IIm) and 2-[(2-Chloro-5-(4-methoxyphenyl)pyridine-3-yl)(hydroxy)methyl]cyclohex-2-en-1-one (IIn).

In yet another embodiment the chloro pyridine skelton based Baylis-Hillman adduct obtained is active against chloroquine sensitive and chloroquine resistant *plasmodium falciparum* strains.

In yet another embodiment the chloro pyridine skelton based Baylis-Hillman adduct obtained exhibits an anti malarial activity against the erythrocytic stage of the malarial parasite.

In yet another embodiment the Hillman adduct obtained is used in a pharmaceutical composition comprising novel anti malarial chloro pyridine skelton based Baylis-Hillman adduct, its derivatives, analogues or salt thereof optionally with pharmaceutically acceptable carriers, adjuvant and additives.

The present invention is predicted on the discovery that certain Baylis Hillman adducts, preferably in substantially pure form has in vitro antimalarial activity and therefore is useful for malaria treatment. The following preferred embodiments are given by way of illustration of the present invention and therefore should not be constructed to limit the scope of the present invention. Synthetic procedures for representative Baylis Hillman adducts Ia-If are disclosed in the present invention are described below.

Scheme-1

GRNERAL SCHEME FOR FORMULAE I:

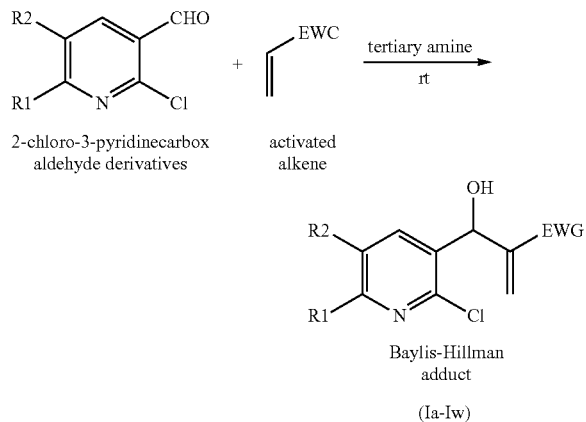

If EWG=CN, the activated alkene is called as acrylonitrile

If EWG=COOMe, the activated alkene is called as methylacrylate

If EWG=COOEt, the activated alkene is called as ethylacrylate

Scheme-2

GENERAL SCHEME FOR FORMULA II

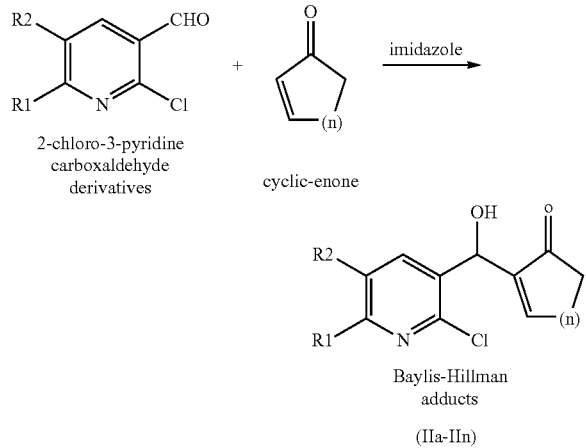

n = 1,2

If n=1, then the cyclic-enone is called as 2-cyclopenten-1-one

If n=2, then the cyclic-enone is called as 2-cyclohexen-1-one

The following examples are given by the way of illustration and therefore should not be construed to limit the scope of the invention Experimental Procedure for the Synthesis of 2-[(2-Chloro-5-methylpyridine-3-yl)(hydroxy)methyl]acrylonitrile (Ia)

To a mixture of 2-Chloro-5-methylpyridinecarboxaldehyde (10 mmol, 1.55 g) and DABCO (10 mmol. 1.12 g) was added an acrylonitrile (60 mmol.) under neat conditions [solvent free conditions] at room temperature and the reaction progress was monitored by TLC. Upon completion of the reaction mixture (~4-5 min.) was diluted with diethyl ether (300 mL) and washed with water 3×50 mL. The organic layer was dried over $Na_2SO_4$ and concentrated, the residue was subjected to column chromatography over silica gel, eluting with ethyl acetate and hexane (2:8, v/v) to give the desired product in almost quantitative (2.05 g).

Experimental Procedure for the Synthesis of 2-[(2-Chloro-5-ethyl pyridine-3-yl)(hydroxy)methyl]acrylonitrile (Ib)

To a mixture of 2-Chloro-5-ethylnicotinaldehyde (10 mmol, 1.69 g) and DABCO (10 mmol. 1.12 g) was added an acrylonitrile (60 mmol.) under neat conditions [solvent free conditions] at room temperature and the reaction progress was monitored by TLC. Upon completion of the reaction mixture (~4-5 min.) was diluted with diethyl ether (300 ml.) and washed with water 3×50 ml. The organic layer was dried over $Na_2SO_4$ and concentrated, the residue was subjected to column chromatography over silica gel, eluting with ethyl acetate and hexane (2:8, v/v) to give the desired product in almost quantitative (2.20 g.).

Experimental Procedure for the Synthesis of 2-[(2-Chloro-5-phenylpyridine-3-yl)(hydroxy)methyl]acrylonitrile (Ic)

To a mixture of 2-Chloro-5-phenylnicotinaldehyde (10 mmol, 2.17 g) and DABCO (10 mmol. 1.12 g) was added an acrylonitrile (60 mmol.) under neat conditions [solvent free conditions] at room temperature and the reaction progress was monitored by TLC. Upon completion of the reaction mixture (~4-5 min.) was diluted with diethyl ether (300 ml.) and washed with water 3×50 ml. The organic layer was dried over $Na_2SO_4$ and concentrated, the residue was subjected to column chromatography over silica gel, eluting with ethyl acetate and hexane (2:8, v/v) to give the desired product in almost quantitative (2.68 g.).

Experimental Procedure for the Synthesis of Methyl 6-chloro-5-(2-cyano-1-hydroxyallyl)2-pyridinecarboxylate (Id)

To a mixture of Methyl 6-chloro-5-formyl-2-pyridincarboxylate (10 mmol, 1.99 g) and DABCO (10 mmol. 1.12 g) was added an acrylonitrile (60 mmol.) under neat conditions [solvent free conditions] at room temperature and the reaction progress was monitored by TLC. Upon completion of the reaction mixture (~4-5 min.) was diluted with diethyl ether (300 ml.) and washed with water 3×50 ml. The organic layer was dried over $Na_2SO_4$ and concentrated, the residue was subjected to column chromatography over silica gel, eluting with ethyl acetate and hexane (2:8, v/v) to give the desired product in almost quantitative (2.50 g.).

Experimental Procedure for the Synthesis of Methyl 2-[(2-chloro-5-methylpyridine-3-)(hydroxy)methyl]acrylate (Ie)

To a mixture of 2-Chloro-5-methylnicotinaldehyde (10 mmol, 1.55 g) and DABCO (10 mmol. 1.12 g) was added an methyl/ethyl acrylate (60 mmol.) under neat conditions [solvent free conditions] at room temperature and the reaction progress was monitored by TLC. Upon completion of the reaction mixture (~5 min.) was diluted with diethyl ether (300 ml.) and washed with water 3×50 ml. The organic layer was dried over $Na_2SO_4$ and concentrated, the residue was subjected to column chromatography over silica gel, eluting with ethyl acetate and hexane (2:8, v/v) to give the desired product in almost quantitative (2.40 g.).

Experimental Procedure for the Synthesis of Methyl 2-[(2-chloro-5-phenylpyridine-3-yl)(hydroxy)methyl]acrylate (If)

To a mixture of 2-Chloro-5-phenylnicotinaldehyde (10 mmol, 2.17 g) and DABCO (10 mmol. 1.12 g) was added an methyl/ethyl acrylate (60 mmol.) under neat conditions [solvent free conditions] at room temperature and the reaction progress was monitored by TLC. Upon completion of the reaction mixture (~5 min.) was diluted with diethyl ether (300 ml.) and washed with water 3×50 ml. The organic layer was dried over $Na_2SO_4$ and concentrated, the residue was subjected to column chromatography over silica gel, eluting with ethyl acetate and hexane (2:8, v/v) to give the desired product in almost quantitative (3.01 g.).

Experimental Procedure for the Synthesis of 2-[(2-chloro-5-n-pentylpyridine-3-yl)(hydroxy)methyl]acrylonitrile (Ig)

To a mixture of 2-Chloro-5-pentylnicotinaldehyde (10 mmol, 2.11 g) and DABCO (10 mmol. 1.12 g) was added an acrylonitrile (60 mmol.) under neat conditions [solvent free conditions] at room temperature and the reaction progress was monitored by TLC. Upon completion of the reaction mixture (~4-5 min.) was diluted with diethyl ether (300 ml.) and washed with water 3×50 ml. The organic layer was dried over $Na_2SO_4$ and concentrated, the residue was subjected to column chromatography over silica gel, eluting with ethyl acetate and hexane (2:8, v/v) to give the desired product in almost quantitative (2.62 g.).

Experimental Procedure for the Synthesis of 2-[(2-Chloro-5-methyl-6-phenylpyridine-3-yl)(hydroxy)methyl]acrylonitrle (Ih)

To a mixture of 2-Chloro-5-methyl-6-phenylnicotinaldehyde (10 mmol, 2.31 g) and DABCO (10 mmol. 1.12 g) was added an acrylonitrile (60 mmol) under neat conditions [solvent free conditions] at room temperature and the reaction progress was monitored by TLC. Upon completion of the reaction mixture (~4-5 min.) was diluted with diethyl ether (300 ml.) and washed with water 3×50 ml. The organic layer was dried over $Na_2SO_4$ and concentrated, the residue was subjected to column chromatography over silica gel, eluting with ethyl acetate and hexane (2:8, v/v) to give the desired product in almost quantitative (2.83 g.).

Experimental Procedure for the Synthesis of Ethyl 6-chloro-5-(2-cyano-1-hydroxyallyl)-2-phenyl-nicotinate (Ii)

To a mixture of 2-Chloro-5-ethoxyacetate)-6-phenylnicotinaldehyde (10 mmol, 2.89 g) and DABCO (10 mmol. 1.12 g) was added an acrylonitrile (60 mmol.) under neat conditions [solvent free conditions] at room temperature and the reaction progress was monitored by TLC. Upon completion of the reaction mixture (~4-5 min.) was diluted with diethyl ether (300 ml.) and washed with water 3×50 ml. The organic layer was dried over $Na_2SO_4$ and concentrated, the residue was subjected to column chromatography over silica gel, eluting with ethyl acetate and hexane (2:8, v/v) to give the desired product in almost quantitative (3.41 g.).

Experimental Procedure for the Synthesis of 2-[(2-Chloro-5-(4-methoxyphenyl)pyridine-3-yl)(hydroxy)methyl]acrylonitrile (Ij)

To a mixture of 2-Chloro-5-(4-methoxyphenyl)-nicotinaldehyde (10 mmol, 2.45 g) and DABCO (10 mmol. 1.12 g) was added an acrylonitrile (60 mmol.) under neat conditions [solvent free conditions] at room temperature and the reaction progress was monitored by TLC. Upon completion of the reaction mixture (~4-5 min.) was diluted with diethyl ether (300 ml.) and washed with water 3×50 ml. The organic layer was dried over $Na_2SO_4$ and concentrated, the residue was subjected to column chromatography over silica gel, eluting with ethyl acetate and hexane (2:8, v/v) to give the desired product in almost quantitative (2.99 g.).

Experimental Procedure for the Synthesis of Methyl 2-[(2-chloro-5-ethylpyridine-3-yl)(hydroxy)methyl]acrylate (Ik)

To a mixture of 2-Chloro-5-ethylnicotinaldehyde (10 mmol, 1.69 g) and DABCO (10 mmol. 1.12 g) was added an methyl/ethyl acrylate (60 mmol.) under neat conditions [solvent free conditions] at room temperature and the reaction progress was monitored by TLC. Upon completion of the reaction mixture (~5 min.) was diluted with diethyl ether (300 ml.) and washed with water 3×50 ml. The organic layer was dried over $Na_2SO_4$ and concentrated, the residue was subjected to column chromatography over silica gel, eluting with ethyl acetate and hexane (2:8, v/v) to give the desired product in almost quantitative (2.54 g.).

Experimental Procedure for the Synthesis of Methyl 2-[(2-chloro-5-n-pentylpyridine-3-yl)(hydroxy)methyl]acrylate (Il)

To a mixture of 2-Chloro-5-pentylnicotinaldehyde (10 mmol, 2.11 g) and DABCO (10 mmol. 1.12 g) was added an methyl/ethyl acrylate (60 mmol.) under neat conditions [solvent free conditions] at room temperature and the reaction progress was monitored by TLC. Upon completion of the reaction mixture (~5 min.) was diluted with diethyl ether (300 ml) and washed with water 3×50 ml. The organic layer was dried over $Na_2SO_4$ and concentrated, the residue was subjected to column chromatography over silica gel, eluting with ethyl acetate and hexane (2:8, v/v) to give the desired product in almost quantitative (2.96 g.).

Experimental Procedure for the Synthesis of Methyl 2-[(2-chloro-5-methyl-6-phenylpyridine-3-yl)(hydroxy)methyl]acrylate (Im)

To a mixture of 2-Chloro-5-methyl-6-phenylnicotinaldehyde (10 mmol, 2.31 g) and DABCO (10 mmol. 1.12 g) was added an methyl/ethyl acrylate (60 mmol.) under neat conditions [solvent free conditions] at room temperature and the reaction progress was monitored by TLC. Upon completion of the reaction mixture (~5 min.) was diluted with diethyl ether (300 ml) and washed with water 3×50 ml. The organic layer was dried over $Na_2SO_4$ and concentrated, the residue was subjected to column chromatography over silica gel, eluting with ethyl acetate and hexane (2:8, v/v) to give the desired product in almost quantitative (3.16 g.).

Experimental Procedure for the Synthesis of Methyl 6-chloro-5-[1-hydroxy-2-(methoxycarbonyl)allyl]pyridine-2-carboxylate (In)

To a mixture of Methyl 6-chloro-5-formyl-2-pyridincarboxylate (10 mmol, 1.99 g) and DABCO (10 mmol. 1.12 g) was added an methyl/ethyl acrylate (60 mmol.) under neat conditions [solvent free conditions] at room temperature and the reaction progress was monitored by TLC. Upon completion of the reaction mixture (~5 min.) was diluted with diethyl ether (300 ml) and washed with water 3×50 ml. The organic layer was dried over $Na_2SO_4$ and concentrated, the residue was subjected to column chromatography over silica gel, eluting with ethyl acetate and hexane (2:8, v/v) to give the desired product in almost quantitative (2.84 g.).

Experimental Procedure for the Synthesis of Ethyl 6-chloro-5-(1-hydroxy-2-(methoxycarbonyl)allyl)-2-phenyl-nicotinate (Io)

To a mixture of 2-Chloro-5-ethoxyacetate)-6-phenylnicotinaldehyde (10 mmol, 2.89 g) and DABCO (10 mmol. 1.12 g) was added an methyl/ethyl acrylate (60 mmol.) under neat conditions [solvent free conditions] at room temperature and the reaction progress was monitored by TLC. Upon completion of the reaction mixture (~5 min.) was diluted with diethyl ether (300 ml) and washed with water 3×50 ml. The organic layer was dried over $Na_2SO_4$ and concentrated, the residue was subjected to column chromatography over silica gel, eluting with ethyl acetate and hexane (2:8, v/v) to give the desired product in almost quantitative (3.74 g.).

Experimental Procedure for the Synthesis of Methyl 2-[(2-chloro-5-(4-methoxy phenyl)pyridine-3-yl)(hydroxy)methyl]acrylate (Ip)

To a mixture of 2-Chloro-5-(4-methoxyphenyl)-nicotinaldehyde (10 mmol, 2.45 g) and DABCO (10 mmol. 1.12 g) was added an methyl/ethyl acrylate (60 mmol.) under neat conditions [solvent free conditions] at room temperature and the reaction progress was monitored by TLC. Upon completion of the reaction mixture (~5 min.) was diluted with diethyl ether (300 ml) and washed with water 3×50 ml. The organic layer was dried over $Na_2SO_4$ and concentrated, the residue was subjected to column chromatography over silica gel, eluting with ethyl acetate and hexane (2:8, v/v) to give the desired product in almost quantitative (3.32 g.).

Experimental Procedure for the Synthesis of Ethyl 2-[(2-chloro-5-methylpyridine-3-)(hydroxy)methyl]acrylate (Iq)

To a mixture of 2-Chloro-5-methylnicotinaldehyde (10 mmol, 1.55 g) and DABCO (10 mmol. 1.12 g) was added an methyl/ethyl acrylate (60 mmol.) under neat conditions [solvent free conditions] at room temperature and the reaction progress was monitored by TLC. Upon completion of the reaction mixture (~5 min.) was diluted with diethyl ether (300 ml) and washed with water 3×50 ml. The organic layer was dried over $Na_2SO_4$ and concentrated, the residue was subjected to column chromatography over silica gel, eluting with ethyl acetate and hexane (2:8, v/v) to give the desired product in almost quantitative (2.54 g.).

Experimental Procedure for the Synthesis of Ethyl 2-[(2-chloro-5-ethylpyridine-3-yl)(hydroxy)methyl]acrylate (Ir)

To a mixture of 2-Chloro-5-ethylnicotinaldehyde (10 mmol, 1.69 g) and DABCO (10 mmol. 1.12 g) was added an methyl/ethyl acrylate (60 mmol.) under neat conditions [solvent free conditions] at room temperature and the reaction progress was monitored by TLC. Upon completion of the reaction mixture (~5 min.) was diluted with diethyl ether (300 ml) and washed with water 3×50 ml. The organic layer was dried over $Na_2SO_4$ and concentrated, the residue was subjected to column chromatography over silica gel, eluting with ethyl acetate and hexane (2:8, v/v) to give the desired product in almost quantitative (2.68 g.).

Experimental Procedure for the Synthesis of Ethyl 2-[(2-chloro-5-phenylpyridine-3-yl)(hydroxy)methyl]acrylate (Is)

To a mixture of 2-Chloro-5-phenylnicotinaldehyde (10 mmol, 2.17 g) and DABCO (10 mmol. 1.12 g) was added an methy/ethyl acrylate (60 mmol.) under neat conditions [solvent free conditions] at room temperature and the reaction progress was monitored by TLC. Upon completion of the reaction mixture (~5 min.) was diluted with diethyl ether (300 ml) and washed with water 3×50 ml. The organic layer was dried over $Na_2SO_4$ and concentrated, the residue was subjected to column chromatography over silica gel, eluting with ethyl acetate and hexane (2:8, v/v) to give the desired product in almost quantitative (316.5 g.).

Experimental Procedure for the Synthesis of Ethyl 2-[(2-chloro-5-methyl-6-phenylpyridine-3-yl)(hydroxy)methyl]acrylate (It)

To a mixture of 2-Chloro-5-methyl-6-phenylnicotinaldehyde (10 mmol, 2.31 g) and DABCO (10 mmol. 1.12 g) was added an methyl/ethyl acrylate (60 mmol.) under neat conditions [solvent free conditions] at room temperature and the reaction progress was monitored by TLC. Upon completion of the reaction mixture (~5 min.) was diluted with diethyl ether (300 ml) and washed with water 3×50 ml. The organic layer was dried over $Na_2SO_4$ and concentrated, the residue was subjected to column chromatography over silica gel, eluting with ethyl acetate and hexane (2:8, v/v) to give the desired product in almost quantitative (3.30 g.).

Experimental Procedure for the Synthesis of Methy-6-chloro-5-[1-hydroxy-2-(ethoxycarbonyl)allyl]pyridine-2-carboxylate (Iu)

To a mixture of Methyl 6-chloro-5-formyl-2-pyridincarboxylate (10 mmol, 1.99 g) and DABCO (10 mmol. 1.12 g) was added an methyl/ethyl acrylate (60 mmol.) under neat conditions [solvent free conditions] at room temperature and the reaction progress was monitored by TLC. Upon completion of the reaction mixture (~5 min.) was diluted with diethyl ether (300 ml) and washed with water 3×50 ml. The organic layer was dried over $Na_2SO_4$ and concentrated, the residue was subjected to column chromatography over silica gel, eluting with ethyl acetate and hexane (2:8, v/v) to give the desired product in almost quantitative (2.98 g.).

Experimental Procedure for the Synthesis of Ethyl 6-chloro-5-(1-hydroxy-2-(ethoxycarbonyl)allyl)-2-phenyl-nicotinate (Iv)

To a mixture of 2-Chloro-5-ethoxyacetate)-6-phenylnicotinaldehyde (10 mmol, 2.89 g) and DABCO (10 mmol. 1.12 g) was added an methyl/ethyl acrylate (60 mmol.) under neat conditions [solvent free conditions] at room temperature and the reaction progress was monitored by TLC. Upon completion of the reaction mixture (~5 min.) was diluted with diethyl ether (300 ml) and washed with water 3×50 ml. The organic layer was dried over $Na_2SO_4$ and concentrated, the residue was subjected to column chromatography over silica gel, eluting with ethyl acetate and hexane (2:8, v/v) to give the desired product in almost quantitative (3.88 g).

Experimental Procedure for the Synthesis of Ethyl 2-[(2-chloro-5-(4-methoxyphenyl)pyridine-3-yl)(hydroxy)methyl]acrylate (Iw)

To a mixture of 2-Chloro-5-(4-methoxyphenyl)-nicotinaldehyde (10 mmol, 2.45 g) and DABCO (10 mmol. 1.12 g) was added an methyl/ethyl acrylate (60 mmol.) under neat conditions [solvent free conditions] at room temperature and the reaction progress was monitored by TLC. Upon completion of the reaction mixture (~5 min.) was diluted with diethyl ether (300 ml) and washed with water 3×50 ml. The organic layer was dried over $Na_2SO_4$ and concentrated, the residue was subjected to column chromatography over silica gel, eluting with ethyl acetate and hexane (2:8, v/v) to give the desired product in almost quantitative (346 g).

Experimental Procedure for the Synthesis of 2-[(2-Chloro-5-methyl pyridine-3-yl)(hydroxy)methyl]cyclopent-2-en-1-one (IIa)

The clear solution of 2-Chloro-5-methylnicotinaldehyde (10 mmol, 1.55 g) and imidazole (10 mmol, 0.68 g) in 50 ml. of MeOH was slowly charged with 50 ml. of deionized water. To a stirred homogeneous reaction mixture was added 2-cyclopenten-1-one (10.2 mmol., 0.88 g) at room temperature and reaction progress was monitored by TLC. Upon completion of the reaction, excess MeOH was removed under reduced pressure, washed with water and extracted with $CHCl_3$ thrice. Combined organic layers were washed with brine solution twice. The organic layer was concentrated and column chromatography of the crude product on silica gel, using 30% EtOAC in hexane as eluent, gave pure Baylis-Hillman adduct in 98% yield (2.32 g)

Experimental Procedure for the Synthesis of 2-[(2-Chloro-5-ethyl pyridine-3-yl)(hydroxy)methyl]cyclopent-2-en-1-one (IIb)

The clear solution of 2-Chloro-5-ethylnicotinaldehyde (10 mmol, 1.69) and imidazole (10 mmol, 0.68 g) in 50 ml. of MeOH was slowly charged with 50 ml. of deionized water. To a stirred homogeneous reaction mixture was added 2-cyclopenten-1-one (10.2 mmol., 0.88 g) at room temperature and reaction progress was monitored by TLC. Upon completion of the reaction, excess MeOH was removed under reduced pressure, washed with water and extracted with $CHCl_3$ thrice. Combined organic layers were washed with brine solution twice. The organic layer was concentrated and column chromatography of the crude product on silica gel, using 30% EtOAC in hexane as eluent, gave pure Baylis-Hillman adduct in 97% yield (2.47 g).

Experimental Procedure for the Synthesis of 2-[(2-Chloro-5-phenyl pyridine-3-yl)(hydroxy)methyl] cyclopent-2-en-1-one (IIc)

The clear solution of 2-Chloro-5-phenylnicotinaldehyde (10 mmol, 2.17 g) and imidazole (10 mmol) in 50 ml. of MeOH was slowly charged with 50 ml. of deionized water. To a stirred homogeneous reaction mixture was added 2-cyclopenten-1-one (10.2 mmol., 0.88 g) at room temperature and reaction progress was monitored by TLC. Upon completion of the reaction, excess MeOH was removed under reduced pressure, washed with water and extracted with $CHCl_3$ thrice. Combined organic layers were washed with brine solution twice. The organic layer was concentrated and column chromatography of the crude product on silica gel, using 30% EtOAC in hexane as eluent, gave pure Baylis-Hillman adduct in 95% yield (2.84 g).

Experimental Procedure for the Synthesis of 2-[(2-Chloro-5-methyl-6-phenyl pyridine-3-yl)(hydroxy) methyl]cyclopent-2-en-1-one (IId)

The clear solution of 2-Chloro-5-methyl-6-phenylnicotinaldehyde (10 mmol, 2.31 g) and imidazole (10 mmol) in 50 ml. of MeOH was slowly charged with 50 ml. of deionized water. To a stirred homogeneous reaction mixture was added 2-cyclopenten-1-one (10.2 mmol., 0.88 g) at room temperature and reaction progress was monitored by TLC. Upon completion of the reaction, excess MeOH was removed under reduced pressure, washed with water and extracted with $CHCl_3$ thrice. Combined organic layers were washed with brine solution twice. The organic layer was concentrated and column chromatography of the crude product on silica gel, using 30% EtOAC in hexane as eluent, gave pure Baylis-Hillman adduct in 93% yield (2.84 g).

Experimental Procedure for the Synthesis of Methyl 6-chloro-5-[hydroxy(5-oxo-1-cyclopentenyl)methyl]-2-pyridinecarboxylate (IIe)

The clear solution of Methyl 6-chloro-5-formyl-2-pyridincarboxylate (10 mmol, 1.99 g) and imidazole (10 mmol) in 50 ml. of MeOH was slowly charged with 50 ml. of deionized water. To a stirred homogeneous reaction mixture was added 2-cyclopenten-1-one (10.2 mmol., 0.88 g) at room temperature and reaction progress was monitored by TLC. Upon completion of the reaction excess MeOH was removed under reduced pressure, washed with water and extracted with $CHCl_3$ thrice. Combined organic layers were washed with brine solution twice. The organic layer was concentrated and column chromatography of the crude product on silica gel, using 30% EtOAC in hexane as eluent, gave pure Baylis-Hillman adduct in 90% yield (2.53 g).

Experimental Procedure for the Synthesis of Ethyl 6-chloro-5-[hydroxy(5-oxo-1-cyclopentenyl)methyl]-2-phenyl nicotinate (IIf)

The clear solution of 2-Chloro-5-ethoxyacetate)-6-phenylnicotinaldehyde (10 mmol, 2.89 g) and imidazole (10 mmol) in 50 ml. of MeOH was slowly charged with 50 ml. of deionized water. To a stirred homogeneous reaction mixture was added 2-cyclopenten-1-one (10.2 mmol. 0.88 g) at room temperature and reaction progress was monitored by TLC. Upon completion of the reaction, excess MeOH was removed under reduced pressure, washed with water and extracted with $CHCl_3$ thrice. Combined organic layers were washed with brine solution twice. The organic layer was concentrated and column chromatography of the crude product on silica gel, using 30% EtOAC in hexane as eluent, gave pure Baylis-Hillman adduct in 88% yield (3.26 g).

Experimental Procedure for the Synthesis of 2-[(2-Chloro-5-(4-methoxyphenyl)pyridine-3-yl)(hydroxy)methyl]cyclopent-2-en-1-one (IIg)

The clear solution of 2-Chloro-5-(4-methoxyphenyl)-nicotinaldehyde (10 mmol, 2.45 g) and imidazole (10 mmol) in 50 ml. of MeOH was slowly charged with 50 ml. of deionized water. To a stirred homogeneous reaction mixture was added 2-cyclopenten-1-one (10.2 mmol. 0.88 g) at room temperature and reaction progress was monitored by TLC. Upon completion of the reaction, excess MeOH was removed under reduced pressure, washed with water and extracted with $CHCl_3$ thrice. Combined organic layers were washed with brine solution twice. The organic layer was concentrated and column chromatography of the crude product on silica gel, using 30% EtOAC in hexane as eluent, gave pure Baylis-Hillman adduct in 90% yield (2.97 g).

Experimental Procedure for the Synthesis of 2-[(2-Chloro-5-methylpyridine-3-yl)(hydroxy)methyl]2-cyclohexene1-one (IIh)

The clear solution of 2-Chloro-5-methylnicotinaldehyde (10 mmol, 1.55 g) and imidazole (10 mmol) in 50 ml. of MeOH was slowly charged with 50 ml. of deionized water. To a stirred homogeneous reaction mixture was added 2-cyclohexen-1-one (10.2 mmol., 1 g) at room temperature and reaction progress was monitored by TLC. Upon completion of the reaction, excess MeOH was removed under reduced pressure, washed with water and extracted with $CHCl_3$ thrice. Combined organic layers were washed with brine solution twice. The organic layer was concentrated and column chromatography of the crude product on silica gel, using 30% EtOAC in hexane as eluent, gave pure Baylis-Hillman adduct in 92% yield (2.22 g).

Experimental Procedure for the Synthesis of 2-[(2-Chloro-5-ethylpyridine-3-yl)(hydroxy)methyl]cyclohex-2-ene-1-one (IIi)

The clear solution of 2-Chloro-5-ethylnicotinaldehyde (10 mmol, 1.69 g) and imidazole (10 mmol) in 50 ml. of MeOH was slowly charged with 50 ml. of deionized water. To a stirred homogeneous reaction mixture was added 2-cyclohexen-1-one (10.2 mmol., 1.0 g) at room temperature and reaction progress was monitored by TLC. Upon completion of the reaction, excess MeOH was removed under reduced pressure, washed with water and extracted with $CHCl_3$ thrice. Combined organic layers were washed with brine solution twice. The organic layer was concentrated and column chromatography of the crude product on silica gel, using 30% EtOAC in hexane as eluent, gave pure Baylis-Hillman adduct in 95% yield (2.43 g).

Experimental Procedure for the Synthesis of 2-[(2-Chloro-5-phenyl pyridine-3-yl)(hydroxy)methyl] cyclohex-2-ene-1-one (IIj)

The clear solution of 2-Chloro-5-phenylnicotinaldehyde (10 mmol, 2.17 g) and imidazole (10 mmol) in 50 ml. of MeOH was slowly charged with 50 ml. of deionized water. To a stirred homogeneous reaction mixture was added 2-cyclohexen-1-one (10.2 mmol., 1.0 g) at room temperature and reaction progress was monitored by TLC. Upon completion of the reaction, excess MeOH was removed under reduced pressure, washed with water and extracted with $CHCl_3$ thrice. Combined organic layers were washed with brine solution twice. The organic layer was concentrated and column chromatography of the crude product on silica gel, using 30% EtOAC in hexane as eluent, gave pure Baylis-Hillman adduct in 95% yield (2.25 g).

Experimental Procedure for the Synthesis of 2-[(2-Chloro-5-methyl-6-phenyl pyridine-3-yl)(hydroxy)methyl]cyclohex-2-ene-1-one (IIk)

The clear solution of 2-chloro-substituted-3-pyridinecarboxyaldehyde (10 mmol 2.31 g) and imidazole (10 mmol) in 50 ml. of MeOH was slowly charged with 50 ml. of deionized water. To a stirred homogeneous reaction mixture was added 2-cyclohexen-1-one (10.2 mmol., 1.0 g) at room temperature and reaction progress was monitored by TLC. Upon completion of the reaction, excess MeOH was removed under reduced pressure, washed with water and extracted with $CHCl_3$ thrice. Combined organic layers were washed with brine solution twice. The organic layer was concentrated and column chromatography of the crude product on silica gel, using 30% EtOAC in hexane as eluent, gave pure Baylis-Hillman adduct in 90% yield (2.93 g).

Experimental Procedure for the Synthesis of Methyl 6-chloro-5-[hydroxy(5-oxo-1-cyclohexenyl)methyl]-2-pyridine carboxylate (III)

The clear solution of Methyl 6-chloro-5-formyl-2-pyridincarboxylate (10 mmol, 1.99 g) and imidazole (10 mmol, 0.68 g) in 50 ml. of MeOH was slowly charged with 50 ml. of deionized water. To a stirred homogeneous reaction mixture was added 2-cyclohexen-1-one (10.2 mmol., 1.0 g) at room temperature and reaction progress was monitored by TLC. Upon completion of the reaction, excess MeOH was removed under reduced pressure, washed with water and extracted with $CHCl_3$ thrice. Combined organic layers were washed with brine solution twice. The organic layer was concentrated and column chromatography of the crude product on silica gel, using 30% EtOAC in hexane as eluent, gave pure Baylis-Hillman adduct in 87% yield (2.56 g).

Experimental Procedure for the Synthesis of Ethyl 6-chloro-5-[hydroxy(5-oxo-1-cyclohexenyl)methyl]-2-phenyl nicotinate (IIm)

The clear solution of 2-Chloro-5-ethoxyacetate)-6-phenylnicotinaldehyde (10 mmol, 2.89 g) and imidazole (10 mmol) in 50 ml. of MeOH was slowly charged with 50 ml. of deionized water. To a stirred homogeneous reaction mixture was added 2-cyclohexen-1-one (10.2 mmol., 1.0 g) at room temperature and reaction progress was monitored by TLC. Upon completion of the reaction, excess MeOH was removed under reduced pressure, washed with water and extracted with $CHCl_3$ thrice. Combined organic layers were washed with brine solution twice. The organic layer was concentrated and column chromatography of the crude product on silica gel, using 30% EtOAC in hexane as eluent, gave pure Baylis-Hillman adduct in 92% yield (3.5 g).

Experimental Procedure for the Synthesis of 2-[(2-Chloro-5-(4-methoxyphenyl)pyridine-3-yl)(hydroxy)methyl]cyclohex-2-en-1-one (IIn)

The clear solution of 2-Chloro-5-(4-methoxyphenyl)-nicotinaldehyde (10 mmol, 2.45 g) and imidazole (10 mmol) in 50 ml. of MeOH was slowly charged with 50 ml. of deionized water. To a stirred homogeneous reaction mixture was added 2-cyclohexen-1-one (10.2 mmol., 1.0 g) at room temperature and reaction progress was monitored by TLC. Upon completion of the reaction, excess MeOH was removed under reduced pressure, washed with water and extracted with $CHCl_3$ thrice. Combined organic layers were washed with brine solution twice. The organic layer was concentrated and column chromatography of the crude product on silica gel, using 30% EtOAc in hexane as eluent, gave pure Baylis-Hillman adduct in 91% yield (3.13 g).

2-[(2-Chloro-5-methyl pyridine-3-yl)(hydroxy)methyl]acrylonitrile (Ia)

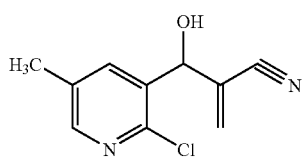

2-[(2-Chloro-5-ethyl pyridine-3-yl)(hydroxy)methyl] acrylonitrile (Ib)

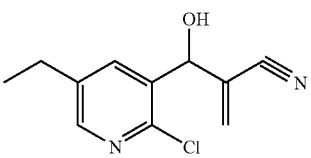

2-[(2-Chloro-5-phenyl pyridine-3-yl)(hydroxy)methyl]acrylonitrile (Ic)

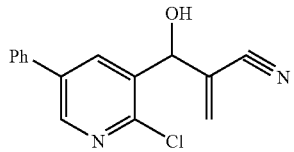

Methyl 6-chloro-5-(2-cyano-1-hydroxy allyl) 2-pyridine carboxylate (Id)

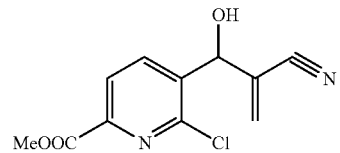

Methyl 2-[(2-chloro-5-methylpyridine-3-)(hydroxy)methyl]acrylate (Ie)

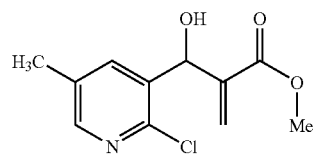

Methyl 2-[(2-chloro-5-phenylpyridine-3-yl)(hydroxy)methyl]acrylate (If)

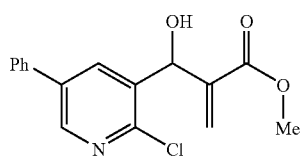

2-[(2-chloro-5-n-pentylpyridine-3-yl)(hydroxy)methyl]acrylonitrile (Ig)

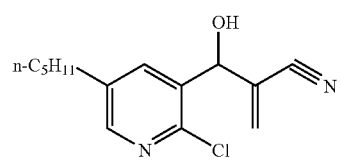

21

2-[(2-Chloro-5-methyl-6-phenyl pyridine-3-yl)(hydroxy)methyl]acrylonitrile (Ih)

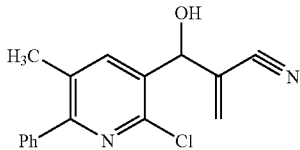

Ethyl 6-chloro-5-(2-cyano-1-hydroxy allyl)-2-phenyl-nicotinate (Ii)

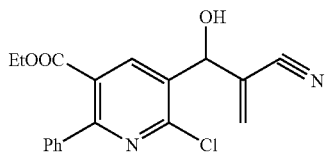

2-[(2-Chloro-5-(4-methoxyphenyl)pyridine-3-yl)(hydroxy)methyl]acrylonitrile (Ij)

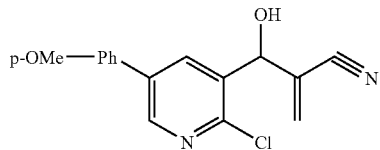

Methyl 2-[(2-chloro-5-ethyl pyridine-3-yl)(hydroxy)methyl]acrylate (Ik)

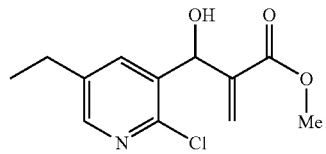

Methyl 2-[(2-chloro-5-n-pentyl pyridine-3-yl)(hydroxy)methyl]acrylate (Il)

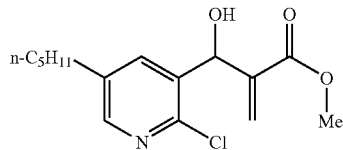

22

Methyl 2-[(2-chloro-5-methyl-6-phenyl pyridine-3-yl)(hydroxy)methyl]acrylate (Im)

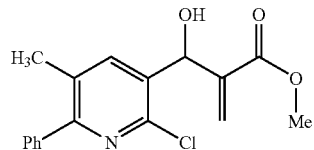

Methyl 6-chloro-5-[1-hydroxy-2-(methoxycarbonyl)allyl]pyridine-2-carboxylate (In)

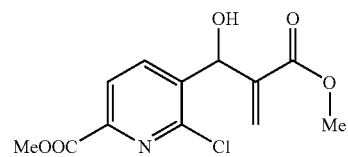

Ethyl 6-chloro-5-(1-hydroxy-2-(methoxycarbonyl)allyl)-2-phenyl-nicotinate (Io)

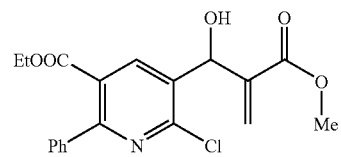

Methyl 2-[(2-chloro-5-(4-methoxy phenyl)pyridine-3-yl)(hydroxy)methyl]acrylate (Ip)

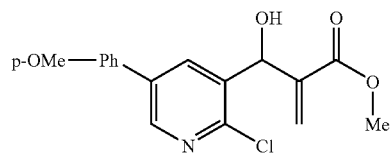

Ethyl 2-[(2-chloro-5-methyl pyridine-3-)(hydroxy)methyl]acrylate (Iq)

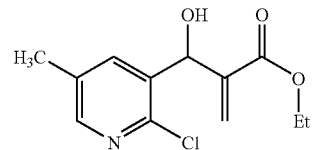

Ethyl 2-[(2-chloro-5-ethyl pyridine-3-yl)(hydroxy)methyl]acrylate (Ir)

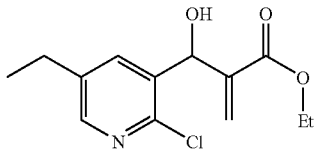

Ethyl 2-[(2-chloro-5-phenyl pyridine-3-yl)(hydroxy)methyl]acrylate (Is)

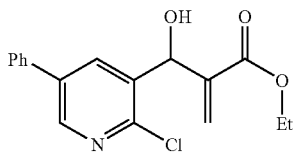

Ethyl 2-[(2-chloro-5-methyl-6-phenyl pyridine-3-yl)(hydroxy)methyl]acrylate (It)

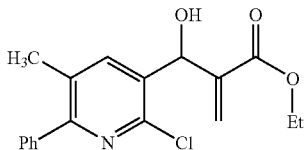

Methyl 6-chloro-5-[1-hydroxy-2-(ethoxycarbonyl)allyl]pyridine-2-carboxylate (Iu)

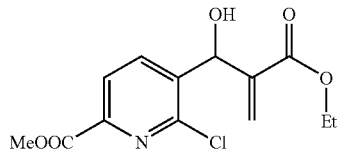

Ethyl 6-chloro-5-(1-hydroxy-2-(ethoxycarbonyl)allyl)-2-phenyl-nicotinate (Iv)

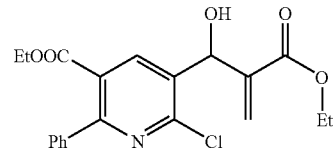

Ethyl 2-[(2-chloro-5-(4-methoxyphenyl)pyridine-3-yl)(hydroxy)methyl]acrylate (Iw)

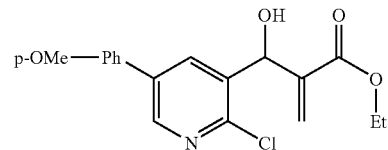

2-[(2-Chloro-5-methyl pyridine-3-yl)(hydroxy)methyl]cyclopent-2-en-1-one (IIa)

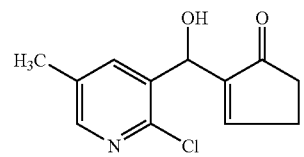

2-[(2-Chloro-5-ethyl pyridine-3-yl)(hydroxy)methyl]cyclopent-2-en-1-one (IIb)

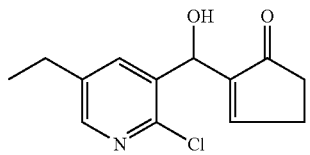

2-[(2-Chloro-5-phenyl pyridine-3-yl)(hydroxy)methyl]cyclopent-2-en-1-one (IIc)

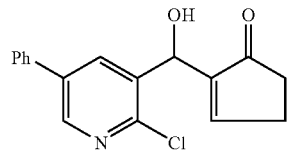

2-[(2-Chloro-5-methyl-6-phenyl pyridine-3-yl)(hydroxy)methyl]cyclopent-2-en-1-one (IId)

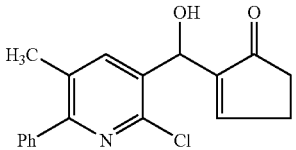

Methyl 6-chloro-5-[hydroxy(5-oxo-1-cyclopentenyl)methyl]-2-pyridine carboxylate (IIe)

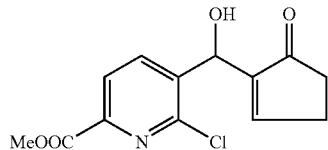

Ethyl 6-chloro-5-[hydroxy(5-oxo-1-cyclopentenyl)methyl]-2-phenyl nicotinate (IIf)

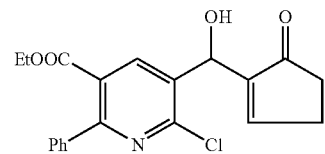

2-[(2-Chloro-5-(4-methoxyphenyl) pyridine-3-yl)(hydroxy)methyl]cyclopent-2-en-1-one (IIg)

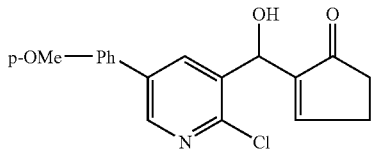

2-[(2-Chloro-5-methyl pyridine-3-yl)(hydroxy)methyl]2-cyclohexen-1-one (IIh)

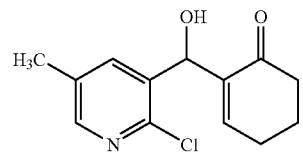

2-[(2-Chloro-5-ethyl pyridine-3-yl)(hydroxy)methyl]cyclohex-2-ene-1-one (IIi)

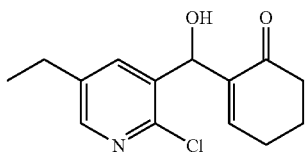

2-[(2-Chloro-5-phenyl pyridine-3-yl)(hydroxy)methyl]cyclohex-2-ene-1-one (IIj)

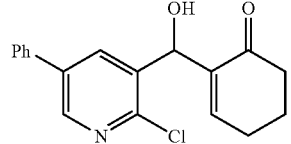

2-[(2-Chloro-5-methyl-6-phenyl pyridine-3-yl)(hydroxy)methyl]cyclohex-2-ene-1-one (IIk)

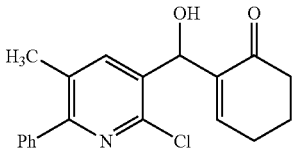

Methyl 6-chloro-5-[hydroxy(5-oxo-1-cyclohexenyl)methyl]-2-pyridine carboxylate (IIl)

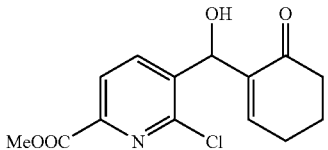

Ethyl 6-chloro-5-[hydroxy(5-oxo-1-cyclohexenyl)methyl]-2-phenyl nicotinate (IIm)

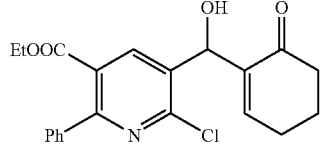

2-[(2-Chloro-5-(4-methoxyphenyl) pyridine-3-yl)(hydroxy)methyl]cyclohex-2-en-1-one (IIn)

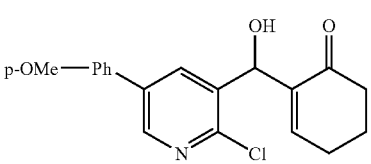

The present invention may be better understood by reference to the following non-limiting Examples, which are provided as exemplary of the invention. The following examples are presented in order to more fully illustrate the preferred embodiments of the invention. Synthetic procedures for representative Baylis Hillman adducts Ia-Iw and IIa-IIn were described below.

Typical Experimental Procedure for Ia to Iw Using EtOH Solvent System:

To a stirred solution of substrate aldehyde (substituted 2-chloro-pyridine-3-carboxyaldehyde) (1 mmol) and DABCO (1,4-diaza bicyclo[2.2.2]ocatane; 100 mol %) in 5 mL of ethanol was added an activated alkene (1.2 mmol) at room temperature and the reaction progress was monitored by TLC. After completion (10 min) of the reaction, the excess solvent was removed under reduced pressure. The obtained residue was diluted with diethyl ether (150 ml.) and brine (50 ml.). After partition, the aqueous layer was extracted with chloroform (2×50 ml.). The combined organic layer was concentrated and the residue was subjected to column chromatography over silicagel, eluting with ethyl acetate and hexane to give the desired product.

Typical Experimental Procedure for Ia to Iw Using Acetonitrile Solvent System:

To a stirred solution of substrate aldehyde (substituted 2-chloro-pyridine-3-carboxyaldehyde) (1 mmol) and DABCO [1,4-diaza bicyclo(2.2.2)ocatane] (100 mol %) in 5 mL of acetonitrile was added an activated alkene (1.2 mmol) at room temperature and the reaction progress was monitored by TLC. After completion (25 min) of the reaction, the excess solvent was removed under reduced pressure. The obtained residue was diluted with diethyl ether (150 ml.) and brine (50 ml.). After partition, the aqueous layer was extracted with chloroform (2×50 ml.). The combined organic layer was concentrated and the residue was subjected to column chromatography over silica gel, eluting with ethyl acetate and hexane to give the desired product in almost quantitative yield.

Typical Experimental Procedure for Ia to Iw Using 1,4-Dioxane Solvent System:

To a stirred solution of substrate aldehyde (substituted 2-chloro-pyridine-3-carboxyaldehyde) (1 mmol) and DABCO [1,4-diaza bicyclo(2.2.2)ocatane] (100 mol %) in 5 mL of 1,4-dioxane was added an activated alkene (1.2 mmol) at room temperature and the reaction progress was monitored by TLC. After completion (12 min) of the reaction, the excess solvent was removed under reduced pressure. The obtained residue was diluted with diethyl ether (150 ml.) and brine (50 ml.). After partition, the aqueous layer was extracted with chloroform (2×50 ml.). The combined organic layer was concentrated and the residue was subjected to column chromatography over silicagel, eluting with ethyl acetate and hexane to give the desired product in almost quantitative yield.

Typical Experimental Procedure for Ia to Iw Using Tetrahydro Furan (THF) Solvent System:

To a stirred solution of substrate aldehyde (substituted 2-chloro-pyridine-3-carboxyaldehyde) (1 mmol) and DABCO [1,4-diaza bicyclo(2.2.2)ocatane] (100 mol %) in 5 mL of THF solvent was added an activated alkene (1.2 mmol) at room temperature and the reaction progress was monitored by TLC. After completion (20 min), of the reaction, the excess solvent was removed under reduced pressure. The obtained residue was diluted with diethyl ether (150 ml.) and brine (50 ml.). After partition, the aqueous layer was extracted with chloroform (2×50 ml.). The combined organic layer was concentrated and the residue was subjected to column chromatography over silicagel, eluting with ethyl acetate and hexane to give the desired product in almost quantitative yield.

Typical Experimental Procedure for Ia to Iw Using Dimethylformamide (DMF) Solvent System:

To a stirred solution of substrate aldehyde (substituted 2-chloro-pyridine-3-carboxyaldehyde) (1 mmol) and DABCO [1,4-diaza bicyclo(2.2.2)ocatane] (100 mol %) in 5 mL of DMF solvent was added an activated alkene (1.2 mmol) at room temperature and the reaction progress was monitored by TLC. After completion of the reaction, the excess solvent was removed under reduced pressure. The obtained residue was diluted with diethyl ether (150 ml.) and brine (50 ml.). After partition (12 min), the aqueous layer was extracted with chloroform (2×50 ml.). The combined organic layer was concentrated and the residue was subjected to column chromatography over silicagel, eluting with ethyl acetate and hexane to give the desired product in almost quantitative yield.

Typical Experimental Procedure for Ia to Iw Using Chloroform Solvent System:

To a stirred solution of substrate aldehyde (substituted 2-chloro-pyridine-3-carboxyaldehyde) (1 mmol) and DABCO [1,4-diaza bicyclo(2.2.2)ocatane] (100 mol %) in 5 mL of chloroform was added an activated alkene (1.2 mmol) at room temperature and the reaction progress was monitored by TLC. After completion (25 min) of the reaction, the excess solvent was removed under reduced pressure. The obtained residue was diluted with diethyl ether (150 ml.) and brine (50 ml.). After partition, the aqueous layer was extracted with chloroform (2×50 ml.). The combined organic layer was concentrated and the residue was subjected to column chromatography over silica gel, eluting with ethyl acetate and hexane to give the desired product in almost quantitative yield.

Typical Experimental Procedure for IIa-IIn Using Aqueous Methanol Solvent System:

The clear solution of aldehyde (1 mmol) and imidazole (100 mol %) in 5 ml. of MeOH was slowly charged with 5 ml. of deionized water. To a stirred homogeneous reaction mixture was added cyclic-enone (1.2 mmol.) at room temperature and reaction progress was monitored by TLC for every 5 mins. After completion of the reaction (within 28-30 min), the excess solvent was removed under reduced pressure. The obtained residue was subjected to column chromatography over silica gel using ethylacetate, hexane (30:70, v/v) as eluting solvent system. The desired product was obtained in 82-98% yield.

Typical Experimental Procedure for IIa-IIn Using Methanol Solvent System:

To a stirred and clear homogeneous solution of aldehyde (1 mmol) and imidazole (100 mol %) in 5 ml. of MeOH was added with cyclic-enone (1.2 mmol.) at room temperature and reaction progress was monitored by TLC for every 5 mins. After completion of the reaction (within 90-120 min), the excess solvent was removed under reduced pressure. The obtained residue was subjected to column chromatography over silica gel using ethylacetate, hexane (30:70, v/v) as eluting solvent system. The desired product was obtained in 82-98% yield.

Typical Experimental Procedure for IIa-IIn Using Aqueous Tetrahydro Furan (aq. THF) Solvent System:

The clear solution of aldehyde (1 mmol) and imidazole (100 mol %) in 5 ml. of THF was slowly charged with 5 ml. of deionized water. To a stirred homogeneous reaction mixture was added cyclic-enone (1.2 mmol.) at room temperature and reaction progress was monitored by TLC for every 5 mins. After completion of the reaction (within 40-60 min), the excess solvent was removed under reduced pressure. The obtained residue was subjected to column chromatography over silica gel using ethylacetate, hexane (30:70, v/v) as eluting solvent system. The desired product was obtained in 82-98% yield.

Typical Experimental Procedure for IIa-IIn Using Aqueous Dimethylformamide (aq. DMF) Solvent System:

The clear solution of aldehyde (1 mmol) and imidazole (100 mol %) in 5 ml. of DMF was slowly charged with 5 ml. of deionized water. To a stirred homogeneous reaction mixture was added cyclic-enone (1.2 mmol.) at room temperature and reaction progress was monitored by TLC for every 5 mins. After completion of the reaction (within 45-60 min), the excess solvent was removed under reduced pressure. The obtained residue was subjected to column chromatography over silica gel using ethylacetate, hexane (30:70, v/v) as eluting solvent system. The desired product was obtained in 82-98% yield.

Spectral Data:

Example Ia

2-[(2-Chloro-5-methylpyridine-3-yl)(hydroxy)methyl]acrylonitrile $^1$H-NMR (CDCl$_3$, 200 MHz): δ 8.2 (d, 1H), 7.78 (d, 1H), 6.08 (s, 1H), 6.09 (s, 1H), 5.64 (s, 1H), 2.40 (s, 1H); $^{13}$C-NMR: (CDCl$_3$, 50 MHz): 148.36, 145.29, 136.96, 132.98, 132.19, 130.29, 124.12, 115.85, 68.60, 16.80; MS (m/z, %): 208, 156, 120, 93, 65, 39. Anal. calcd. for C$_{10}$H$_9$ClN$_2$O: C, 57.57%; H, 4.34%; N, 13.43%. Found: C, 57.85%; H, 4.68%; N, 13.52%.

Example Ib

2-[(2-Chloro-5-ethylpyridine-3-yl)(hydroxy)methyl]acrylonitrile $^1$H-NMR (CDCl$_3$, 200 MHz): δ 8.18 (d, 1H), 7.82 (d, 1H), 6.1 (s, 1H), 6.08 (s, 1H), 5.66 (s, 1H), 2.72 (q, 2H), 1.3 (t, 3H); $^{13}$C-NMR: (CDCl$_3$, 50 MHz): δ 148.67, 146.36, 139.52, 136.92, 133.34, 131.59, 124.47, 116.22, 70.06, 25.34, 14.80; MS (EI) m/z: 222 (M$^+$), 170, 134, 106, 77, 51. Anal. calcd. for C$_{11}$H$_{11}$ClN$_2$O: C, 59.31%; H, 5.02%; N, 12.58%. Found: C, 59.70%; H, 5.33%; N, 12.75%.

Example Ic

2-[(2-Chloro-5-phenylpyridine-3-yl)(hydroxy)methyl]acrylonitrile $^1$H-NMR (CDCl$_3$, 200 MHz): δ 8.58 (d, 1H), 8.2 (d, 1H), 7.4-7.6 (m, 5H), 6.14 (s, 1H), 6.1 (s, 1H), 5.66 (s, 1H). $^{13}$C-NMR: (CDCl$_3$, 50 MHz): δ 70.37, 116.18, 124.13, 127.18, 128.78, 129.27, 132.05, 133.33, 135.57, 135.94, 136.82, 147.68; MS (EI) m/z: 270 (M+), 245, 218, 182, 154, 141, 77; Anal. calcd. for C$_{15}$H$_{11}$ClN$_2$O: C, 66.53%; H, 4.13%; N, 10.34%. Found: C, 66.67%; H, 4.38%; N, 10.70%.

Example Id

Methyl 6-chloro-5-(2-cyano-1-hydroxyprop-2-en-1-yl)pyridine-2-carboxylate $^1$H-NMR (CDCl$_3$, 200 MHz): δ 8.15 (d, 1H), 8.22 (d, 1H), 6.1 (d, 2H), 5.73 (d, 1H), 3.98 (s, 3H); $^{13}$C-NMR: (CDCl$_3$, 50 MHz): δ 164.05, 149.01, 147.33, 138.36, 137.96, 132.63, 124.42, 123.52, 115.98, 69.99, 53.19; MS (EI) m/z: 252 (M+), 222, 200, 194, 164, 112, 76, 59. Anal. calcd. for C$_{11}$H$_9$ClN$_2$O$_3$: C, 52.29%; H, 3.59%; N, 11.09%. Found: C, 52.56%; H, 3.68%; N, 11.34%.

Example Ie

Methyl 2-[(2-chloro-5-methylpyridine-3-yl)(hydroxy)methyl]acrylate $^1$H-NMR (CDCl$_3$, 200 MHz): δ 8.11 (d, 1H), 7.71 (d, 1H), 6.32 (s, 1H), 5.8 (s, 1H), 5.56 (s, 1H), 3.8 (s, 3H), 2.35 (s, 3H); $^{13}$C-NMR (CDCl$_3$, 50 MHz): δ 166.06, 148.17, 146.52, 140.25, 137.85, 134.85, 132.44, 126.73, 67.89, 51.70, 17.34; MS (m/z, %): 241, 206, 156, 120, 92, 65. Anal. calcd. for C$_{11}$H$_{12}$ClNO$_3$: C, 54.68%; H, 4.99%; N, 5.80%. Found: C, 54.86%; H, 5.10%; N, 5.98%.

Example If

Methyl 2-[(2-chloro-5-phenylpyridine-3-yl)(hydroxy)methyl]acrylate $^1$H-NMR (CDCl$_3$, 200 MHz): δ 8.48 (d, 1H), 8.12 (d, 1H), 7.34-7.58 (m, 5H), 6.34 (s, 1H), 5.88 (s 1H), 5.62 (s, 1H), 4.18 (b, 1H), 3.77 (s, 3H); $^{13}$C-NMR: (CDCl$_3$, 50 MHz): δ 166.60, 148.39, 146.67, 139.91, 136.23, 136.06, 135.70, 135.13, 129.08, 128.44, 127.49, 127.00, 68.98, 52.13; MS (EI) m/z: 303 (M+), 268, 236, 218, 182, 153, 127, 115, 77, 55. Anal. calcd. for C$_{16}$H$_{14}$ClNO$_3$: C, 63.24%; H, 4.68%; N, 4.61%. Found: C, 63.42%; H, 4.88%; N, 4.86%.

Ig:

2-[(2-Chloro-5-n-pentylpyridine-3-yl)(hydroxy)methyl]acrylonitrile $^1$H-NMR (CDCl$_3$, 200 MHz): δ 8.18 (s, 1H), 7.8 (s, 1H), 6.45 (s, 1H), 6.5 (s, 1H), 5.62 (s, 1H), 2.62 (t, 2H), 1.23-1.65 (m, 6H), 0.95 (t, 3H); MS EI (m/z): 264 (M+), 212, 176, 41; Anal. calcd. for C$_{14}$H$_{17}$ClN$_2$O: C, 63.51%; H, 6.47%; N, 10.58%. Found: C, 63.96%; H, 6.88%; N, 10.92%

Ih:

2-[(2-Chloro-5-methyl-6-phenylpyridine-3-yl)(hydroxy)methyl]acrylonitrile

1H-NMR (CDCl$_3$, 200 MHz): δ 7.82 (s, 1H), 7.35-7.55 (m, 5H), 6.07 (s, 1H), 6.1 (s, 1H), 5.62 (s, 1H), 2.4 (s, 3H); $^{13}$C-NMR: (CDCl$_3$, 50 MHz): δ 158.71, 145.64, 139.69, 138.23, 131.72, 130.98, 128.81, 128.64, 128.25, 124.19, 116.36, 69.67, 19.27; MS (EI) m/z: 284 (M+), 232, 196, 168, 119, 77, 52, 39. Anal. calcd. for C$_{16}$H$_{13}$ClN$_2$O: C, 67.48%; H, 4.60%; N, 9.84%. Found: C, 67.69%; H, 4.82%; N, 10.01%.

Ii:

Ethyl 6-chloro-5-(2-cyano-1-hydroxy allyl)-2-phenyl-nicotinate $^1$H-NMR (CDCl$_3$, 200 MHz): δ 8.82 (s, 1H), 7.6 (m, 2H), 7.42 (m, 3H), 6.04 (s, 2H), 5.63 (s, 1H), 5.4 (b, 1H), 4.21 (q, 2H), 1.25 (t, 3H); MS (EI) m/z: 342 (M+), 307, 262, 254, 179, 77; Anal. calcd. for C$_{18}$H$_{15}$ClN$_2$O$_3$: C, 63.07%; H, 4.41%; N, 8.17%. Found: C, 62.88%; H, 4.65%; N, 8.47%.

Ij:

2-{[2-Chloro-5-(4-methoxyphenyl)-pyridine-3-yl](hydroxy)methyl}acrylonitrile $^1$H-NMR (CDCl$_3$, 200 MHz): δ 8.5 (s, 1H), 8.12 (s, 1H), 7.5 (m, 2H), 6.95 (m, 2H), 6.11 (d, 2H), 5.71 (s, 1H), 3.84 (s, 3H); $^{13}$C-NMR: (CDCl$_3$, 50 MHz): δ 160.23, 147.08, 136.39, 135.00, 133.34, 131.96, 128.26, 124.15, 116.26, 114.72, 70.23, 55.38; MS (EI) m/z: 300 (M+), 248, 212, 185, 107, 65; Anal. calcd. for C$_{16}$H$_{13}$ClN$_2$O$_2$: C, 63.90%; H, 4.36%; N, 9.31%. Found: C, 64.01%; H, 4.54%; N, 9.46%.

Ik:

Methyl 2-[(2-chloro-5-ethylpyridine-3-yl)(hydroxy)methyl]acrylate $^1$H-NMR (CDCl$_3$, 200 MHz): δ 8.15 (d, 1H), 7.77 (d, 1H), 6.32 (s, 1H), 5.81 (s, 1H), 5.51 (s, 1H), 3.81 (s, 3H), 2.7 (q, 3H), 1.3 (t, 3H); $^{13}$C-NMR: (CDCl$_3$, 50 MHz): δ 167.39, 149.27, 147.78, 140.28, 139.62, 137.77, 129.62, 126.34, 69.79, 51.60, 25.76, 14.72; MS (EI) m/z: 222 (M+), 187, 173, 102, 65; Anal. calcd. for C$_{12}$H$_{14}$ClNO$_3$: C, 56.37%, H, 5.52%, N, 5.19%. Found: C, 56.78%, H, 5.89%, N, 5.62%.

Il:

Methyl 2-[(2-chloro-5-n-pentylpyridine-3-yl)(hydroxy)methyl]acrylate $^1$H-NMR (CDCl$_3$, 200 MHz): δ 8.1 (s, 1H), 7.68 (s, 1H), 6.22 (s, 1H), 5.78 (s, 1H), 5.23 (s, 1H), 3.78 (s, 3H), 2.58 (t, 2H), 1.2-1.65 (m, 6H), 0.9 (t, 3H); $^{13}$C-NMR: (CDCl$_3$, 50 MHz): δ 166.59, 148.29, 146.86, 140.06, 137.50, 134.62, 127.19, 68.80, 52.02, 32.11, 31.12, 30.46, 22.24, 13.93, 13.80; MS (EI) m/z: 297 (M+), 282, 224, 189, 155, 71; Anal. calcd. for. C$_{15}$H$_{20}$ClNO$_3$: C, 60.50%; H, 6.77%; N, 4.70%. Found: C, 60.56%; H, 6.89%; N, 4.85%.

Im:

Methyl 2-[(2-chloro-5-methyl-6-phenylpyridine-3-yl)(hydroxy)methyl]acrylate $^1$H-NMR (CDCl$_3$, 200 MHz): δ 7.78 (s, 1H), 7.35-7.55 (m, 5H), 6.37 (s, 1H), 5.82 (s, 1H), 5.65 (s, 1H), 3.82 (b, 1H), 2.4 (s, 3H); $^{13}$C-NMR: (CDCl$_3$, 50 MHz): δ 166.69, 157.90, 146.34, 139.94, 139.77, 138.68, 133.03, 130.22, 128.94, 128.35, 128.12, 127.34, 68.91, 52.11, 19.33; MS (EI) m/z: 317 (M+), 302, 2282, 250, 230, 196, 167, 141, 117; Anal. calcd. for C$_{17}$H$_{16}$ClNO$_3$: C, 64.26%; H, 5.07%; N, 4.41%. Found: C, 64.77%; H, 5.24%; N, 4.52%.

In:

Methyl 6-chloro-5 [1-hydroxy-2-(methoxycarbonyl)prop-2-en-1-yl]pyridine-2-carboxylate $^1$H-NMR (CDCl$_3$, 200 MHz): δ 8.12 (m, 2H), 6.32 (s, 1H), 5.82 (s, 1H), 5.52 (s, 1H), 3.98 (s, 3H), 3.78 (s, 3H); $^{13}$C-NMR: (CDCl$_3$, 50 MHz): δ 166.44, 164.30, 149.60, 147.02, 139.43, 138.26, 127.81, 124.00, 69.09, 52.99, 52.21; MS (EI) m/z: 285 (M+), 250, 217, 197, 164, 140, 115, 83, 59; Anal. calcd. for C$_{12}$H$_{12}$ClNO$_5$: C, 50.45%; H, 4.23%; N, 4.41%. Found: C, 50.89%; H, 4.44%; N, 4.67%.

Io:

Ethyl 6-chloro-5-(1-hydroxy-2-(methoxycarbonyl)allyl)-2-phenyl-nicotinate $^1$H-NMR (CDCl$_3$, 200 MHz): δ 8.8 (s, 1H), 7.62 (m, 2H), 7.4 (m, 3H), 6.41 (s, 1H), 5.98 (s, 1H), 5.78 (s, 1H), 4.2 (q, 2H), 3.68 (s, 3H), 1.25 (t, 3H); $^{13}$C-NMR: (CDCl$_3$, 50 MHz) 165.57, 156.43, 149.39, 140.64, 139.61, 137.86, 133.07, 129.35, 128.99, 128.38, 128.28, 127.65, 67.95, 62.17, 52.14, 29.58, 13.55; MS (EI) m/z: 375 (M+), 330, 313, 299, 257, 165, 77; Anal. calcd. for: C$_{19}$H$_{18}$ClNO$_5$: C, 60.73%; H, 4.83%; N, 3.72%. Found: C, 60.89%; H, 4.99%; N, 3.87%.

Ip:

Methyl 2-{[2-chloro-5-(4-methoxyphenyl)-pyridine-3-yl](hydroxy)methyl}acrylate $^1$H-NMR (CDCl$_3$, 200 MHz): δ 8.49 (s, 1H), 8.1 (s, 1H), 7.5 (m, 2H), 6.98 (m, 2H), 6.38 (s, 1H), 5.9 (s, 1H), 5.65 (s, 1H), 3.85 (s, 3H), 3.8 (s, 3H); $^{13}$C-NMR: (CDCl$_3$, 50 MHz): δ 166.61, 160.00, 147.58, 146.17, 139.88, 135.70, 135.19, 135.00, 128.12, 127.48, 114.80, 114.57, 68.96, 60.33, 55.30, 52.14, 24.58; MS (EI) m/z: 333 (M+), 299, 273, 248, 212, 170, 141, 99, 43; Anal. calcd. for C$_{17}$H$_{16}$ClNO$_4$: C, 61.18%; H, 4.83%; N, 4.20%. Found: C, 61.45%; H, 4.99%; N, 4.67%.

Iq:

Ethyl2-[(2-chloro-5-methylpyridine-3-yl)(hydroxy)methyl]acrylate $^1$H-NMR (CDCl$_3$, 200 MHz): 8.06 (d, 1H), 7.66 (d, 1H), 6.28 (s, 1H), 5.76 (s, 1H), 5.55 (s, 1H), 4.16 (q, 2H), 2.30 (s, 3H), 1.25 (t, 3H); $^{13}$C-NMR: (CDCl$_3$, 50 MHz): δ 166.30, 148.83, 148.89, 140.15, 137.98, 134.49, 132.70, 127.37, 127.08, 69.08, 61.23, 17.70, 14.06; MS EI (m/z): 255 (M$^+$), 220, 192, 154, 146, 120, 92, 65. Anal. calcd. for C$_{12}$H$_{14}$ClNO$_3$: C, 56.35%; H, 5.55%; N, 5.48%. Found: C, 56.66%; H, 5.74%; N, 5.62%.

Ir:

Ethyl 2-[(2-chloro-5-ethylpyridine-3-yl)(hydroxy)methyl]acrylate $^1$H-NMR (CDCl$_3$, 200 MHz): δ 8.13 (d, 1H), 7.66 (d, 1H), 6.28 (s, 1H), 5.75 (s, 1H), 5.28 (s, 1H), 4.25 (q, 2H), 2.64 (q, 2H), 1.2o (t, 3H); $^{13}$C-NMR: (CDCl$_3$, 50 MHz): δ 167.65, 151.26, 147.68, 140.32, 139.62, 136.73, 128.75, 125.36, 70.78, 60.92, 25.96, 17.12, 14.12; MS EI (m/z): 269 (M$^+$), 234, 204, 166, 132, 104, 79; Anal. calcd. for C$_{13}$H$_{16}$ClNO$_3$: C, 57.89%; H, 5.98%; N, 4.2%. Found: C, 58.12%; H, 6.22%; N, 4.36%.

Is:

Ethyl 2-[(2-chloro-5-phenylpyridine-3-yl)(hydroxy)methyl]acrylate $^1$H-NMR (CDCl$_3$, 200 MHz): δ 8.5 (d, 1H), 8.12 (s, 1H), 7.35-7.6 (m, 5H), 6.34 (s, 1H), 5.88 (s, 1H), 5.62 (s, 1H), 4.3 (q, 2H), 3.88 (b, 1H), 1.3 (t, 3H); $^{13}$C-NMR: (CDCl$_3$, 50 MHz): δ 166.65, 148.89, 147.12, 140.62, 136.74, 136.54, 136.18, 135.65, 129.55, 128.90, 127.61, 127.47, 69.61, 61.68, 14.43; MS (EI) m/z: 317 (M+), 302, 282, 268, 254, 216, 182, 153, 127, 115, 77, 55. Anal. calcd. for C$_{17}$H$_{16}$ClNO$_3$: C, 64.26%; H, 5.07%; N, 4.40%. Found: C, 64.53%; H, 5.25%; N, 4.62%.

It:

Ethyl 2-[(2-chloro-5-methyl-6-phenylpyridine-3-yl)(hydroxy)methyl]acrylate $^1$H-NMR (CDCl$_3$, 200 MHz): 7.78 (s, 1H), 7.35-7.55 (m, 5H), 6.38 (s, 1H), 5.82 (s, 1H), 5.62 (s, 1H), 4.25 (q, 2H), 2.4 (s, 3H), 1.33 (t, 3H); δ $^{13}$C-NMR: (CDCl$_3$, 50 MHz): δ 167.65, 156.35, 145.87, 140.87, 138.67, 137.67, 135.42, 129.87, 127.93, 127.56, 124.42, 70.91, 54.64, 20.12, 14.56; MS (EI) m/z: 331 (M+), 302, 231, 165, 77; Anal. calcd. for C$_{18}$H$_{18}$ClNO$_3$: C, 65.16%; H, 5.47%; N, 4.22%. Found: C, 65.45%; H, 4.56%; N, 4.44%;

Iu:

Methyl 6-chloro-5[1-hydroxy-2-(ethoxycarbonyl)prop-2-en-1-yl]pyridine-2-carboxylate $^1$H-NMR (CDCl$_3$, 200 MHz): δ 8.12 (sharp q, 2H), 6.32, (s, 1H), 5.85 (s, 1H), 5.52 (s, 1H), 4.25 (q, 2H), 3.98 (s, 1H), 3.70 (b, 1H), 1.32 (t, 3H); $^{13}$C-NMR: (CDCl$_3$, 50 MHz): δ 165.79, 164.20, 149.58, 146.75, 139.81, 139.75, 138.20, 127.32, 123.89, 68.77, 61.16, 52.89, 13.85;

MS (EI) m/z: 299 (M+), 264, 219, 178, 129; Anal. calcd. for C$_{13}$H$_{14}$ClNO$_5$: C, 52.10%; H, 4.71%; N, 4.67%. Found: C, 52.43%; H, 4.97%; N, 4.86%.

Iv:

Ethyl 6-chloro-5-(1-hydroxy-2-(ethoxycarbonyl)allyl)-2-phenyl-nicotinate $^1$H-NMR (CDCl$_3$, 200 MHz): δ 8.8 (s, 1H), 7.61 (m, 2H), 7.4 (m, 3H), 6.40 (s, 1H), 5.99 (s, 1H), 5.77 (s, 1H), 4.25 (q, 2H), 4.2 (q, 2H), 1.32 (t, 3H), 1.25 (t, 3H); MS (EI) m/z: 389 (M+), 354, 306, 209, 165, 77; Anal. calcd. for C$_{20}$H$_{20}$ClNO$_5$: C, 61.61%; H, 5.17%; N, 3.59%. Found: C, 61.89%; H, 5.64%; N, 3.82%.

Iw:

Ethyl 2-{[2-chloro-5-(4-methoxyphenyl)-pyridine-3-yl](hydroxy)methyl}acrylate $^1$H-NMR (CDCl$_3$, 200 MHz): δ 8.48 (s, 1H), 8.12 (s, 1H), 7.5 (m, 2H), 6.98 (m, 2H), 6.39 (s, 1H), 5.91 (s, 1H), 5.66 (s, 1H), 4.25 (q, 2H), 1.32 (t, 3H); MS (EI) m/z: 347 (M+), 312, 213, 239, 181, 176, 107, 65; Anal. calcd. for C$_{18}$H$_{18}$ClNO$_4$: C, 62.16%; H, 5.22%; N, 4.03%. Found: C, 62.28%; H, 5.56%; N, 4.23%.

IIa:

2-[(2-Chloro-5-methylpyridine-3-yl)(hydroxy)methyl]cyclopent-2-en-1-one $^1$H-NMR (CDCl$_3$, 200 MHz): δ 8.16 (d, 1H), 7.82 (d, 1H), 7.14 (sharp t, 1H), 5.78 (s, 1H), 4.18 (d, 1H), 2.65 (m, 2H), 2.52 (m, 2H), 2.4 (s, 3H); $^{13}$C-NMR: (CDCl$_3$, 50 MHz): δ 209.59, 160.53, 148.72, 146.06, 144.98, 137.62, 134.93, 132.85, 65.65, 35.07, 26.69, 17.73; MS EI (m/z): 237 (M$^+$), 202, 156, 117, 92, 39. Anal. calcd. for C$_{12}$H$_{12}$ClNO$_2$: C, 60.61%; H, 5.13%; N, 5.89%. Found: C, 60.80%; H, 5.23%; N, 5.98%.

IIb:

2-[(2-Chloro-5-ethylpyridine-3-yl)(hydroxy)methyl]cyclopent-2-en-1-one $^1$H-NMR (CDCl$_3$, 200 MHz): δ 8.18 (d, 1H), 7.78 (d, 1H), 7.21 (t, 1H), 5.58 (s, 1H), 4.25 (b, 1H), 2.66 (q, 2H), 2.4 (m, 2H), 2.54 (m, 2H), 1.29 (t, 3H); $^{13}$C-NMR: (CDCl$_3$, 50 MHz): δ 207.82, 150.62, 149.74, 148.54, 139.76, 138.28, 133.21, 128.66, 65.42, 38.92, 25.88, 23.25, 14.95; MS EI (m/z): 251 (M$^+$), 216, 170, 131, 104, 53; Anal. calcd. for C$_{13}$H$_{14}$ClNO$_2$: C, 62.03%; H, 5.61%; N, 5.56%. Found: C, 62.44%, H, 5.98%; N, 14.56%.

IIc:

2-[(2-Chloro-5-phenylpyridine-3-yl)(hydroxy)methyl]cyclopent-2-en-1-one $^1$H-NMR (CDCl$_3$, 200 MHz): δ 8.53 (s, 1H), 8.21 (s, 1H), 7.36-7.55 (m, 5H), 7.19 (sharp t, 1H), 5.85 (s, 1H), 2.46-2.72 (m, 4H); $^{13}$C-NMR: (CDCl$_3$, 50 MHz): δ 205.82, 152.12, 149.75, 138.92, 138.48, 136.18, 130.14, 125.51, 124.91, 59.77, 45.08, 23.55; MS (EI) m/z: 299 (M+), 264, 236, 153, 77; Anal. calcd. for C$_{17}$H$_{14}$ClNO$_2$: C, 68.18%; H, 4.70%; N, 4.67%. Found: C, 68.24%; H, 4.83%; N, 4.87%.

IId:

2-[(2-Chloro-5-methyl-6-phenylpyridine-3-yl)(hydroxy)methyl]cyclopent-2-en-1-one $^1$H-NMR (CDCl$_3$, 200 MHz): δ 7.85 (s, 1H), 7.35-7.55 (m, 5H), 7.25 (sharp t, 1H), 5.82 (s, 1H), 4.09 (d, 1H), 2.62-2.68 (m, 2H), 2.48-2.55 (m, 2H), 2.4 (s, 3H); $^{13}$C-NMR: (CDCl$_3$, 50 MHz): δ 210.02, 160.43, 157.93, 145.54, 144.70, 139.45, 138.81, 133.34, 130.44, 128.97, 128.39, 128.19, 66.19, 35.11, 26.72, 19.39; MS (EI) m/z: 313 (M+), 278, 50, 235, 193, 115, 77; Anal. calcd. for C$_{18}$H$_{16}$ClNO$_2$: C, 68.90%; H, 5.14%; N, 4.46%. Found: C, 69.12%; H, 5.43%; N, 4.76%.

IIe:

Methyl-6-chloro-5-[hydroxy(5-oxo-cyclopent-1-en-1-yl)methyl]pyridine-2-carboxylate $^1$H-NMR (CDCl$_3$, 200 MHz): δ 8.13 (d, 1H), 8.25 (d, 1H), 7.22 (sharp t, 1H), 5.88 (s, 1H), 3.98 (s, 3H), 2.65 (m, 2H), 2.5 (m, 2H); $^{13}$C-NMR: (CDCl$_3$, 50 MHz): δ 199.93, 164.33, 149.16, 148.69, 146.77, 139.95, 138.26, 123.94, 68.52, 52.93, 38.23, 25.74, 22.25; MS (EI) m/z: 281 (M+), 246, 218, 202, 188, 122, 69; Anal. calcd. for C$_{13}$H$_{12}$ClNO$_4$: C, 55.43%; H, 4.29%; N, 4.97%. Found: C, 55.67%; H, 4.67%; N, 5.14%.

IIf:

Ethyl 6-chloro-5-[hydroxy(5-oxo-1-cyclopentenyl)methyl]-2-phenyl nicotinate $^1$H-NMR (CDCl$_3$, 200 MHz): δ 8.9 (s, 1H), 7.6 (m, 2H), 7.42 (m, 3H), 7.22 (t, 1H), 5.92 (s, 1H), 4.2 (q, 2H), 2.65 (m, 2H), 2.5 (t, 2H), 1.1 (t, 3H); $^{13}$C-NMR: (CDCl$_3$, 50 MHz): δ 205.82, 167.64, 149.25, 149.18, 139.80, 139.22, 136.43, 134.40, 132.7, 129.11, 128.36, 123.26, 117.75, 60.49, 57.2, 45.02, 23.25, 14.35; MS (EI) m/z: 371 (M+), 336, 318, 275, 263, 178, 77; Anal. calcd. for C$_{20}$H$_{18}$ClNO$_4$: C, 64.61%; H, 4.88%; N, 3.77%. Found: C, 64.92%; H, 5.09%; N, 3.78%.

IIg:

2-[(2-Chloro-5-(4-methoxyphenyl) pyridine-3-yl)(hydroxy)methyl]cyclopent-2-en-1-one $^1$H-NMR (CDCl$_3$, 200 MHz): δ 8.43 (d, 1H), 8.13 (d, 1H), 7.49 (m, 2H), 7.18 (t, 1H), 6.92 (m, 3H), 5.8 (s, 1H), 3.82 (s, 3H), 2.53 (m, 2H), 2.45 (m, 2H); MS (EI) m/z: 329 (M+), 294, 276, 251, 107, 65; Anal. calcd. for C$_{18}$H$_{16}$ClNO$_3$: C, 65.56%; H, 4.89%; N, 4.25%. Found: C, 65.87%; H, 5.12%; N, 4.45%.

IIh:

2-[(2-Chloro-5-methylpyridine-3-yl)(hydroxy)methyl]cyclohex-2-en-1-one $^1$H-NMR (CDCl$_3$, 200 MHz): δ 8.1 (d, 1H), 7.78 (d, 1H), 6.46 (t, 1H), 5.72 (s, 1H), 2.5 (m, 2H), 2.36 (s, 3H), 2.38 (m, 2H), 2.03 (m, 2H); $^{13}$C-NMR: (CDCl$_3$, 50 MHz): δ 200.24, 148.49, 148.22, 138.70, 137.95, 134.73, 132.55, 68.37, 38.34, 25.74, 22.35, 17.70; MS EI (m/z): 251 (M+), 216, 198, 116, 84, 65, 48. Anal. calcd. for C$_{13}$H$_{14}$ClNO$_2$: C, 62.01%; H, 5.64%; N, 5.56. Found: C, 62.24%; H, 5.74%; N, 5.68%.

IIi:

2-[(2-Chloro-5-ethylpyridine-3-yl)(hydroxy)methyl]cyclohex-2-ene-1-one $^1$H-NMR (CDCl$_3$, 200 MHz): δ 8.14 (d, 1H), 7.76 (d, 1H), 6.5 (t, 1H), 5.72 (s, 1H), 4.22 (b, 1H), 2.64 (q, 2H), 2.5 (m, 2H), 2.38 (m, 2H), 2.02 (m, 2H), 1.18 (t, 3H); $^{13}$C-NMR: (CDCl$_3$, 50 MHz): δ 200.23, 149.42, 148.86, 139.06, 138.76, 135.32, 134.17, 128.13, 67.75, 38.03, 25.86, 25.78, 22.34, 14.95; MS (m/z, %): 265, 230, 212, 130, 98, 79, 62; Anal. calcd. for C$_{14}$H$_{16}$ClNO$_2$: C, 63.28%; H, 6.07%; N, 5.27%. Found: C, 63.54%, H, 6.42%; N, 5.44%.

IIj:

2-[(2-Chloro-5-phenylpyridine-3-yl)(hydroxy)methyl]cyclohex-2-en-1-one $^1$H-NMR (CDCl$_3$, 200 MHz): δ 8.5 (s, 1H), 8.2 (s, 1H), 7.34-7.64 (m, 5H), 6.5 (t, 1H), 5.8 (s, 1H), 3.85 (b, 1H), 2.05 (m, 2H), 2.35-2.6 (m, 4H); $^{13}$C-NMR: (CDCl$_3$, 50 MHz): δ 200.29, 148.46, 148.00, 146.42, 138.64, 136.41, 136.01, 135.79, 135.39, 129.07, 128.39, 127.06, 68.53, 38.33, 25.76, 22.34. MS (EI) m/z: 313 (M+), 278, 260, 217, 71, 57; Anal. calcd. for C$_{18}$H$_{16}$ClNO$_2$: C, 68.90%; H, 5.14%; N, 4.46%. Found: C, 69.12%; H, 5.27%; N, 4.48%.

IIk:

2-[(2-Chloro-5-methyl-6-phenylpyridine-3-yl)(hydroxy)methyl]cyclohex-2-en-1-one $^1$H-NMR (CDCl$_3$, 200 MHz): δ 7.85 (s, 1H), 7.35-7.55 (m, 5H), 6.66 (t, 1H), 5.75 (s, 1H), 3.86 (d, 1H), 2.5 (m, 2H), 2.4 (m, 2H), 2.4 (s, 3H), 2.0 (m, 2H); $^{13}$C-NMR: (CDCl$_3$, 50 MHz): δ 200.29, 148.46, 148.00, 146.42, 138.64, 136.41, 136.01, 135.79, 135.39, 129.07, 128.39, 127.06, 68.53, 38.33, 25.76, 22.34; MS (EI) m/z: 327 (M+), 311, 291, 273, 249, 218, 117; Anal. calcd. for C$_{19}$H$_{18}$ClNO$_2$: C, 69.62%; H, 5.53%; N, 4.27%. Found: C, 70.07%; H, 5.74%; N, 4.56%.

IIl:

Methyl-6-chloro-5-[hydroxy(6-oxo-cyclohex-1-en-1-yl)methyl]pyridine-2-carboxylate $^1$H-NMR (CDCl$_3$, 200 MHz): δ 8.12 (d, 2H), 8.02 (d, 1H), 6.52 (t, 1H), 5.83 (s, 1H), 3.98 (s, 3H), 2.5 (m, 2H), 2.4 (m, 2H), 2.05 (m, 2H); $^{13}$C-NMR: (CDCl$_3$, 50 MHz): δ 199.93, 164.33, 149.16, 148.69, 146.77, 139.95, 138.26, 123.94, 68.53, 52.93, 38.23, 25.74, 22.25; MS (EI) m/z: 295 (M+), 260, 232, 229, 201, 160, 112, 59; Anal. calcd. for C$_{14}$H$_{14}$ClNO$_4$: C, 56.86%; H, 4.77%; N, 4.74%. Found: C, 57.12%; H, 4.98%; N, 4.98%.

IIm:

Ethyl 6-chloro-5-[hydroxy(5-oxo-1-cyclohexenyl)methyl]-2-phenyl nicotinate $^1$H-NMR (CDCl$_3$, 200 MHz): δ 8.92 (s, 1H), 7.6 (m, 2H), 7.4 (m, 3H), 6.59 (t, 1H), 5.98 (s, 1H), 4.2 (q, 2H), 2.38-2.57 (m, 4H), 2.02 (m, 2H), 1.1 (t, 3H); MS (EI) m/z: 385 (M+), 350, 332, 321, 278, 165, 73; Anal. calcd. for C$_{21}$H$_{20}$ClNO$_4$: C, 65.37%; H, 5.22%; N, 3.63%. Found: C, 65.78%; H, 5.67%; N, 3.78%.

IIn:

2-[(2-Chloro-5-(4-methoxyphenyl)pyridine-3-yl)(hydroxy)methyl]cyclohex-2-en-1-one $^1$H-NMR (CDCl$_3$, 200 MHz): δ 8.45 (s, 1H), 8.13 (s, 1H), 7.5 (d, 2H), 6.95 (d, 2H), 6.55 (t, 1H), 5.78 (s, 1H), 3.82 (s, 3H), 2.3-2.6 (m, 4H), 2.02 (m, 2H); MS (EI) m/z: 343 (M+), 308, 290, 247, 107, 65; Anal. calcd. for C$_{19}$H$_{18}$ClNO$_3$: C, 66.38%; H, 5.28%; N, 4.07%. Found: C, 66.97%; H, 5.56%; N, 4.34%.

Antimalarial Activity:

Parasites were cultured in O (+) erythrocytes in RPMI-1640 media supplemented with 25 mM HEPES buffer and 10% AB (+) serum by candlejar technique.[9] Initial culture was maintained in small vials (2.5 cm dia.) with 10% haematocrit, i.e. 10 µl erythrocytes containing 1.5% ring stage parasite in 100 µl complete media. The culture volume per well for the assay was 100 µl. Parasitamia was determined for each set of culture, number of parasites for the assay were adjusted at 1 to 1.5% by diluting with fresh O (+) RBC. Assay was done in 96 well microtitre flat-bottomed tissue culture plates. Parasite culture was synchronized at ring forms using density gradient method[10] and cultured for 24 h. in the presence of various doses of compounds and chloroquine for their effect in schizont maturation. Test was done in duplicate wells for each dose of the drugs. Control culture was done with RPMI-164 containing 10% AB (+) serum. Growth of the parasites from duplicate wells of each concentration was monitored in JSB stained[11] blood smears by counting number of schizont per 200 asexual parasites. Percent schizont maturation inhibition was calculated by the formula: $(1-N_t/N_c) \times 100$ where, $N_t$ and $N_c$ represent the number of schizont in the test and control well respectively. The effects on parasite growth by the compounds (Ia-If) of the present invention, together with data are shown in tables 1 and 2 respectively.

TABLE 1

Antimalarial activities, $IC_{50}$ and $IC_{90}$ of compounds Ia-If against Chloroquine sensitive (CQS) *P. falciparum* strain
Inhibitory activity in µg/ml

| Compounds | IC50 | | IC90 | |
| --- | --- | --- | --- | --- |
| | SMI | PGI | SMI | PGI |
| Ia | 1.25 | 1.3 | 25.5 | 85 |
| Ib | 1.8 | 4 | 15.5 | 31 |
| Ic | 3.6 | 8 | 25.5 | 23 |
| Id | 3.4 | 7 | 22 | 29 |
| Ie | 18 | 28.5 | 32 | 115 |
| If | 45 | 115 | 125 | 350 |

SMI: Schizont maturation inhibition determined after 24 hr.
PGI: Total parasite growth inhibition determined after 48 hr.

TABLE 2

Antimalarial activities, $IC_{50}$ and $IC_{90}$ of compounds Ia-If against Chloroquine resistant (CQR) *P. falciparum* strain
Inhibitory activity in µg/ml

| Compounds | IC50 | | IC90 | |
| --- | --- | --- | --- | --- |
| | SMI | PGI | SMI | PGI |
| Ia | 22.5 | 10.5 | 125 | 300 |
| Ib | 2.5 | 5.5 | 6.5 | 26 |
| Ic | 0.9 | 2.2 | 1.5 | 6.75 |
| Id | 5.75 | 6.75 | 25.5 | 29 |
| Ie | 3.05 | 5.75 | 7 | 27.5 |
| If | 5 | 10.75 | 30 | 77.5 |

SMI: Schizont maturation inhibition determined after 24 hr.
PGI: Total parasite growth inhibition determined after 48 hr.

We claim:

1. A chloro pyridine skeleton based Baylis-Hillman adduct compound having formula I or II

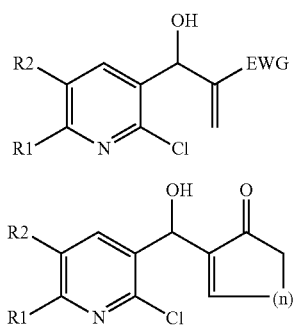

wherein R1 is selected from the group consisting of hydrogen, phenyl and carbomethoxy; R2 is selected from the group consisting of hydrogen, alkyl, $CH_3$, $C_2H_5$, phenyl, n-$C_5H_{11}$, carboethoxy and p-OMe-Ph; and EWG is an electron withdrawing group selected from the group consisting of CN, COOMe and COOEt; and n=1 or 2; or a derivative, analogue or salt thereof.

2. A novel chloro pyridine skeleton based Baylis-Hillman adduct compound as claimed in claim 1 selected from the group consisting of 2-[(2-Chloro-5-methyl pyridine-3-yl)(hydroxy)methyl]acrylonitrile, 2-[(2-Chloro-5-ethyl pyridine-3-yl)(hydroxy)methyl 2]acrylonitrile, 2-[(2-Chloro-5-phenylpyridine-3-yl) (hydroxy)methyl]acrylonitrile, methyl 6-chloro-5-(2-cyano-1-hydroxy allyl)2-pyridine carboxylate, Methyl 2-[(2-chloro-5-methylpyridine-3-)(hydroxy)methyl]acrylate, Methyl 2-[(2-chloro-5-phenylpyridine-3-yl)(hydroxy)methyl]acrylate, 2-[(2-chloro-5-n-pentylpyridine-3-yl)(hydroxy)methyl]acrylonitrile, 2-[(2-Chloro-5-methyl-6-phenyl pyridine-3-yl)(hydroxy)methyl]acrylonitrle, Ethyl 6-chloro-5-(2-cyano-1-hydroxy allyl)-2-phenyl-nicotinate, 2-[(2-Chloro-5-(4-methoxyphenyl) pyridine-3-yl) (hydroxy)methyl]acrylonitrile, Methyl 2-[(2-chloro-5-ethyl pyridine-3-yl)(hydroxy)methyl]acrylate, Methyl 2-[(2-chloro-5-n-pentyl pyridine-3-yl)(hydroxy)methyl]acrylate, Methyl 2-[(2-chloro-5-methyl-6-phenyl pyridine-3-yl)(hydroxy)methyl]acrylate, Methyl 6-chloro-5-[1-hydroxy-2-(methoxycarbonyl)allyl]pyridine-2-carboxylate, Ethyl 6-chloro-5-(1-hydroxy-2-(methoxycarbonyl)allyl)-2-phenyl-nicotinate, Methyl 2-[(2-chloro-5-(4-methoxyphenyl)pyridine-3-yl)(hydroxy)methyl]acrylate, Ethyl 2-[(2-chloro-5-methyl pyridine-3-)(hydroxy)methyl]acrylate, Ethyl 2-[(2-chloro-5-ethyl pyridine-3-yl)(hydroxy)methyl] acrylate, Ethyl 2-[(2-chloro-5-phenyl pyridine-3-yl)(hydroxy)methyl]acrylate, Ethyl 2-[(2-chloro-5-methyl-6-phenyl pyridine-3-yl)(hydroxy)methyl]acrylate, Methyl-6-chloro-5-[1-hydroxy-2-(ethoxycarbonyl)allyl]pyridine-2-carboxylate, Ethyl 6-chloro-5-(1-hydroxy-2-(ethoxycarbonyl)allyl)-2-phenyl-nicotinate, Ethyl 2-[(2-chloro-5-(4-methoxyphenyl)pyridine-3-yl)(hydroxy) methyl]acrylate, 2-[(2-Chloro-5-methyl pyridine-3-yl)(hydroxy)methyl]cyclopent-2-en-1-one, 2-[(2-Chloro-5-ethyl pyridine-3-yl)(hydroxy)methyl]cyclopent-2-en-1-one, 2-[(2-Chloro-5-phenyl pyridine-3-yl)(hydroxy)methyl]cyclopent-2-en-1-one, 2-[(2-Chloro-5-methyl-6-phenyl pyridine-3-yl)(hydroxy)methyl]cyclopent-2-en-1-one, Methyl-6-chloro-5-[hydroxy(5-oxo-1-cyclopentenyl)methyl]-2-pyridine carboxylate, Ethyl 6-chloro-5-[hydroxy(5-oxo-1-cyclopentenyl)methyl]-2-phenyl nicotinate, 2-[(2-Chloro-5-(4-methoxyphenyl)pyridine-3-yl)(hydroxy)methyl] cyclopent-2-en-1-one, 2-[(2-Chloro-5-methyl pyridine-3-yl)(hydroxy)methyl]2-cyclohexene1-one, 2-[(2-Chloro-5-ethyl pyridine-3-yl)(hydroxy)methyl]cyclohex-2-ene-1-one, 2-[(2-Chloro-5-phenyl pyridine-3-yl)(hydroxy)methyl]cyclohex-2-ene-1-one, Methyl 2-[(2-chloro-5-ethyl pyridine-3-yl)(hydroxy)methyl]acrylate, Methyl 6-chloro-5-[hydroxy (5-oxo-1-cyclohexenyl)methyl]-2-pyridine carboxylate, Ethyl 6-chloro-5-[hydroxy(5-oxo-1-cyclohexenyl)methyl]-2-phenyl nicotinate and 2-[(2-Chloro-5-(4-methoxyphenyl) pyridine-3-yl)(hydroxy)methyl]cyclohex-2-en-1-one.

3. A chloro pyridine skeleton based Baylis-Hillman adduct compound as claimed in claim 1, wherein the adduct compound is active against chloroquine sensitive and chloroquine resistant *plasmodium falciparum* strains.

4. A chloro pyridine skeleton based Baylis-Hillman adduct compound as claimed in claim 1, wherein the adduct compound exhibits an anti malarial activity against an erythrocytic stage of a malarial parasite.

5. A pharmaceutical composition comprising the chloro pyridine skeleton based Baylis-Hillman adduct compound as claimed in claim 1, or a derivative, analogue, salt or mixture thereof.

6. A pharmaceutical composition as claimed in claim 5, further comprising one or more pharmaceutically acceptable carriers, adjuvants or additives.

7. A method for the treatment of malaria in a subject, comprising administering to the subject the chloro pyridine skeleton based Baylis-Hillman adduct compound claimed in claim 1.

8. The method of claim 7, wherein a dose of 1-45 µg/ml of the chloro pyridine skeleton based Baylis-Hillman adduct compound is administered to such subject, whereby IC50 against a chloroquine sensitive (CQS) *P. falciparum* strain for schizont maturation inhibition (SMI) determined after 24 hours is achieved.

9. The method of claim 7, wherein a dose of 1-115 µg/ml of the chloro pyridine skeleton based Baylis-Hillman adduct compound is administered to such subject, whereby IC50 against a CQS *P. falciparum* strain for total parasite growth inhibition (PGI) determined after 48 hours is achieved.

10. The method of claim 7, wherein a dose of 25-125 µg/ml of the chloro pyridine skeleton based Baylis-Hillman adduct compound is administered to such subject, whereby IC90 against a chloroquine sensitive (CQS) *P. falciparum* strain for schizont maturation inhibition (SMI) determined after 24 hours is achieved.

11. The method of claim 7, wherein a dose of 85-350 µg/ml of the chloro pyridine skeleton based Baylis-Hillman adduct compound is administered to such subject, whereby IC90 against a CQS *P. falciparum* strain for PGI determined after 48 hours is achieved.

12. The method of claim 7, wherein a dose of 0.2-30 µg/ml of the chloro pyridine skeleton based Baylis-Hillman adduct compound is administered to such subject, whereby IC50 against a chloroquine resistant *plasmodium falciparum* strain for schizont maturation inhibition (SMI) determined after 24 hours is achieved.

13. The method of claim 7, wherein a dose of 5-15 µg/ml of the chloro pyridine skeleton based Baylis-Hillman adduct compound is administered to such subject, whereby IC50 against a chloroquine resistant *plasmodium falciparum* strain for total parasite growth inhibition (PGI) determined after 48 hours is achieved.

14. The method of claim 7, wherein a dose of 1-125 µg/ml of the chloro pyridine skeleton based Baylis-Hillman adduct compound is administered to such subject, whereby IC90 against a chloroquine resistant *plasmodium falciparum* strain for schizont maturation inhibition (SMI) determined after 24 hours is achieved.

15. The method of claim 7, wherein a dose of 25-300 µg/ml of the chloro pyridine skeleton based Baylis-Hillman adduct compound is administered to such subject, whereby IC90 against a chloroquine resistant *plasmodium falciparum* strain for total PGI determined after 48 hours is achieved.

16. A process for the preparation of chloro pyridine skeleton based Baylis-Hillman adduct compound having formula I or II

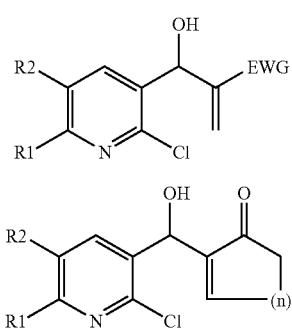

wherein R1 is selected from the group consisting of hydrogen, phenyl and carbomethoxy; R2 is selected from the group consisting of hydrogen, alkyl, $CH_3$, $C_2H_5$, phenyl, n-$C_5H_{11}$, carboethoxy and p-OMe-Ph; EWG is an electron withdrawing group selected from the group consisting of CN, COOMe and COOEt; and n=1 or 2, which comprises reacting 2-chloro-5 and/or 6-substituted 3-pyridine carboxyaldehyde with an activated alkene or cyclic enone, optionally in the presence of aqueous or non aqueous organic solvent, in the presence of a catalyst, at a temperature in the range of 20-30° C. to obtain a reaction mixture having an organic layer, washing the organic layer with water or brine solution, followed by drying and purifying to obtain the adduct compound.

17. The process of claim 16, wherein the 2-chloro-5 and/or 6-substituted 3-pyridine carboxyaldehyde is selected from the group consisting of 2-chloro-5-methylpyridinecarboxyaldehyde, 2-chloro-5-ethylnicotinaldehyde, 2-chloro-5-phenylnicotinaldehyde, methyl 6-chloro-5-formyl-2-pyridincarboxylate, 2-chloro-5-methylnicotinaldehyde, 2-chloro-5-phenylnicotinaldehyde, 2-chloro-5-pentylnicotinaldehyde, 2-chloro-5-methyl-6-phenylnicotinaldehyde, 2-chloro-(5-ethoxyacetate)-6-phenylnicotinaldehyde, 2-chloro-5-(4-methoxyphenyl)-nicotinaldehyde, 2-chloro-5-ethylnicotinaldehyde, 2-chloro-5-pentylnicotinaldehyde, 2-chloro-5-methyl-6-phenylnicotinaldehyde, methyl 6-chloro-5-formyl-2-pyridincarboxylate, 2-chloro-(5-ethoxyacetate)-6-phenylnicotinaldehyde, 2-chloro-5-(4-methoxyphenyl)-nicotinaldehyde, 2-chloro-5-methyl nicotinaldehyde, 2-chloro-5-ethylnicotinaldehyde, 2-chloro-5-phenylnicotinaldehyde, 2-chloro-5-methyl-6-phenylnicotinaldehyde, methyl 6-chloro-5-formyl-2-pyridincarboxylate, 2-chloro-(5-ethoxyacetate)-6-phenylnicotinaldehyde, 2-chloro-5-(4-methoxyphenyl)-nicotinaldehyde, 2-chloro-5-methylnicotinaldehyde, 2-chloro-5-ethylnicotinaldehyde, 2-chloro-5-phenylnicotinaldehyde, 2-chloro-5-methyl-6-phenylnicotinaldehyde, methyl 6-chloro-5-formyl-2-pyridincarboxylate, 2-chloro-(5-ethoxyacetate)-6-phenylnicotinaldehyde, 2-chloro-5-(4-methoxyphenyl)-nicotinaldehyde, 2-chloro-5-methylnicotinaldehyde, 2-chloro-5-ethylnicotinaldehyde, 2-chloro-5-phenylnicotinaldehyde, 2-chloro-substituted-3-pyridinecarboxyaldehyde, methyl 6-chloro-5-formyl-2-pyridincarboxylate, 2-chloro-(5-ethoxyacetate)-6-phenyl nicotinaldehyde and 2-chloro-5-(4-methoxyphenyl)-nicotinaldehyde.

18. A process as claimed in claim 16, wherein the activated alkene is selected from the group consisting of acrylonitrile, methyl acrylate and ethyl acrylate.

19. A process as claimed in claim 16, wherein the cyclic enone is selected from 2-cyclopenten-1-one and 2-cyclohexen-1-one.

20. A process as claimed in claim 16, wherein the catalyst is selected from di azabicylooctane (DABCO) and imidazole.

21. A process as claimed in claim 16, wherein the organic solvent is selected from the group consisting of methanol, ethanol, acetonitrile, tetrahydrofuran, dimethylsulphoxide (DMSO) and dimethylformamide (DMF) 1,4-dioxane, chloroform and sulpholane.

22. A process as claimed in claim 16, wherein the molar ratio of 2-chloro-5 and/or 6-substituted 3-pyridine carboxyaldehyde to activated alkene or cyclic enone is in the range of 1:1 to 1:8.

23. A process as claimed in claim 16, wherein the molar ratio of 2-chloro-5 and/or 6-substituted 3-pyridine carboxyaldehyde to activated alkene in the reaction mixture is in the range of 1:5 to 1:8.

24. A process as claimed in claim 16, wherein the molar ratio of 2-chloro-5 and/or 6-substituted 3-pyridine carboxyaldehyde to cyclic enone is in the range of 1:1 to 1:2.

25. A process as claimed in claim 16, wherein the molar ratio of 2-chloro-5 and/or 6-substituted 3-pyridine carboxyaldehyde to catalyst is in the range of 1:1 to 1:2.

26. A process as claimed in claim 16, wherein the molar ratio of activated alkene to catalyst is in the range of 1:1 to 1:2.

27. A process as claimed in claim 16, wherein the reaction mixture is diluted with diethyl ether and washed with water, and wherein the organic layer is dried over sodium sulphate before subjected to purification by column chromatography.

28. A process as claimed in claim 16, wherein the reaction mixture of aldehyde and cyclic-enone used is taken into chloroform, the organic layer is washed with brine solution before drying and purification to obtain the adduct.

29. A process as claimed in claim 16, wherein the reaction lime between aldehyde and cyclic-enone is in the range of 20-40 minutes.

30. A process as claimed in claim 16, wherein the yield of the product chloro pyridine skeleton based Baylis-Hillman adduct compound is in the range of 85-98% without forming side products.

31. A process as claimed in claim 16, wherein the chloro pyridine skeleton based Baylis-Hillman adduct compound is selected from the group consisting of 2-[(2-Chloro-5-methyl pyridine-3-yl)(hydroxy)methyl]acrylonitrile, 2-[(2-Chloro-5-ethyl pyridine-3-yl)(hydroxy)methyl]acrylonitrile, 2-[(2-Chloro-5-phenylpyridine-3-yl)(hydroxy)methyl]acrylonitrile, methyl 6-chloro-5-(2-cyano-1-hydroxy allyl)2-pyridine carboxylate, Methyl 2-[(2-chloro-5-methylpyridine-3-)(hydroxy)methyl]acrylate, Methyl 2-[(2-chloro-5-phenylpyridine-3-yl)(hydroxy)methyl]acrylate, 2-[(2-chloro-5-n-pentylpyridine-3-yl)(hydroxy)methyl]acrylonitrile, 2-[(2-Chloro-5-methyl-6-phenyl pyridine-3-yl)(hydroxy)methyl]acrylonitrle, Ethyl 6-chloro-5-(2-cyano-1-hydroxy allyl)-2-phenyl-nicotinate, 2-[(2-Chloro-5-(4-methoxyphenyl)pyridine-3-yl)(hydroxy)methyl]acrylonitrile, Methyl 2-[(2-chloro-5-ethyl pyridine-3-yl)(hydroxy)methyl]acrylate, Methyl 2-[(2-chloro-5-n-pentyl pyridine-3-yl)(hydroxy)methyl]acrylate, Methyl 2-[(2-chloro-5-methyl-6-phenyl pyridine-3-yl)(hydroxy)methyl]acrylate, Methyl 6-chloro-5-[1-hydroxy-2-(methoxycarbonyl) allyl]pyridine-2-carboxylate, Ethyl 6-chloro-5-(1-hydroxy-2-(methoxycarbonyl)allyl)-2-phenyl-nicotinate, Methyl 2-[(2-chloro-5-(4-methoxyphenyl)pyridine-3-yl)(hydroxy)methyl]acrylate, Ethyl 2-[(2-chloro-5-methyl pyridine-3-)(hydroxy)methyl]acrylate, Ethyl 2-[(2-chloro-5-ethyl pyridine-3-yl)(hydroxy)methyl] acrylate, Ethyl 2-[(2-chloro-5-phenyl pyridine-3-yl)(hydroxy)methyl]acrylate, Ethyl 2-[(2-chloro-5-methyl-6-phenyl pyridine-3-yl)(hydroxy)methyl]acrylate, Methyl-6-chloro-5-[1-hydroxy-2-(ethoxycarbonyl)allyl]pyridine-2-carboxylate, Ethyl 6-chloro-5-(1-hydroxy-2-(ethoxycarbonyl)allyl)-2-phenyl-nicotinate, Ethyl 2-[(2-chloro-5-(4-meth oxyphenyl)pyridine-3-yl)(hydroxy) methyl]acrylate, 2-[(2-Chloro-5-methyl pyridine-3-yl)(hydroxy)methyl]cyclopent-2-en-1-one, 2-[(2-Chloro-5-ethyl pyridine-3-yl)(hydroxy)methyl]cyclopent-2-en-1-one, 2-[(2-Chloro-5-phenyl pyridine-3-yl)(hydroxy)methyl]cyclopent-2-en-1-one, 2-[(2-Chloro-5-methyl-6-phenyl pyridine-3-yl)(hydroxy)methyl]cyclopent-2-en-1-one, Methyl-6-chloro-5-[hydroxy(5-oxo-1-cyclopentenyl)methyl]-2-pyridine carboxylate, Ethyl 6-chloro-5-[hydroxy(5-oxo-1-cyclopentenyl)methyl]-2-phenyl nicotinate, 2-[(2-Chloro-5-(4-methoxyphenyl)pyridine-3-yl)(hydroxy)methyl] cyclopent-2-en-1-one, 2-[(2-Chloro-5-methyl pyridine-3-yl)(hydroxy)methyl]2-cyclohexene1-one, 2-[(2-Chloro-5-ethyl pyridine-3-yl)(hydroxy)methyl]cyclohex-2-ene-1-one, 2-[(2-Chloro-5-phenyl pyridine-3-yl)(hydroxy)methyl]cyclohex-2-ene-1-one, Methyl 2-[(2-chloro-5-ethyl pyridine-3-yl)(hydroxy)methyl]acrylate, Methyl 6-chloro-5-[hydroxy(5-oxo-1-cyclohexenyl)methyl]-2-pyridine carboxylate, Ethyl 6-chloro-5-[hydroxy(5-oxo-1-cyclohexenyl)methyl]-2-phenyl nicotinate and 2-[(2-Chloro-5-(4-methoxyphenyl) pyridine-3-yl)(hydroxy)methyl]cyclohex-2-en-1-one.

32. A process as claimed in claim 16, wherein the chloro pyridine skeleton based Baylis-Hillman adduct compound obtained is active against chloroquine sensitive and chloroquine resistant *plasmodium falciparum* strains.

33. A process as claimed in claim 16, wherein the chloro pyridine skeleton based Baylis-Hillman adduct compound obtained exhibits an anti malarial activity against the erythrocytic stage of the malarial parasite.

34. A process as claimed in claim 16, further comprising contacting the chloro pyridine skeleton based Baylis-Hillman adduct compound or a derivative, analogue, or salt thereof, or mixture thereof, with one or more pharmaceutically acceptable carriers, adjuvants or additives, to prepare a pharmaceutical composition.

\* \* \* \* \*

UNITED STATES PATENT AND TRADEMARK OFFICE
CERTIFICATE OF CORRECTION

PATENT NO. : 7,666,883 B2  Page 1 of 1
APPLICATION NO. : 11/366672
DATED : February 23, 2010
INVENTOR(S) : Narender et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 778 days.

Signed and Sealed this

Seventh Day of December, 2010

David J. Kappos
*Director of the United States Patent and Trademark Office*